US010053238B1

(12) United States Patent
Schilling

(10) Patent No.: US 10,053,238 B1
(45) Date of Patent: Aug. 21, 2018

(54) FIXTURE, SYSTEM, AND METHOD FOR TESTING LOADS IN A FLEXIBLE AERODYNAMIC MEMBER

(71) Applicant: The Boeing Company, Chicago, IL (US)

(72) Inventor: Kenneth P. Schilling, West Chester, PA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/438,739

(22) Filed: Feb. 21, 2017

(51) Int. Cl.
*B64F 5/60* (2017.01)
*G01M 99/00* (2011.01)
*G01N 3/20* (2006.01)

(52) U.S. Cl.
CPC ............. *B64F 5/60* (2017.01); *G01M 99/007* (2013.01); *G01N 3/20* (2013.01); *G01N 2203/0075* (2013.01); *G01N 2203/0617* (2013.01)

(58) Field of Classification Search
CPC ....... B64F 5/60; G01M 5/005; G01M 99/007; G01M 13/00; G01N 3/20; G01B 21/20; G01B 5/20; G01B 5/00
USPC .................................................. 73/802, 660
See application file for complete search history.

(56) References Cited

U.S. PATENT DOCUMENTS

| | | | | |
|---|---|---|---|---|
| 3,232,349 A | * | 2/1966 | Ballauer ................. | B64C 27/54 415/132 |
| 3,720,387 A | * | 3/1973 | Foote ...................... | B64C 27/54 244/17.25 |
| 4,146,967 A | | 4/1979 | Rohner et al. | |
| 4,195,966 A | * | 4/1980 | Cornelius ............. | B64C 27/625 416/18 |
| 8,857,265 B2 | | 10/2014 | Silva | |
| 9,751,624 B2 | * | 9/2017 | Schank ................... | B64C 27/64 |
| 2006/0257261 A1 | | 11/2006 | Zientek | |

OTHER PUBLICATIONS

European Patent Office Extended European Search Report, dated May 11, 2018, for counterpart foreign application No. EP 17203923.2, Applicant The Boeing Company, 8 pages.

* cited by examiner

*Primary Examiner* — Harshad R Patel
*Assistant Examiner* — Octavia Hollington

(57) ABSTRACT

A fixture, system, and method are provided for testing one or more axial loads in a flexible aerodynamic member. The fixture has a structural frame assembly with a first end portion, a second end portion, and an intermediate portion. The fixture has a first pivotal linkage assembly pivotable about a pitch axis, a pair of pitch actuators to apply a pitch moment to the first pivotal linkage assembly, a second pivotal linkage assembly pivotable about a flap axis, and a pair of flap actuators to apply a flap bending moment to the second pivotal linkage assembly. The fixture has a third pivotal linkage assembly pivotable about the pitch axis, and has a pair of chord actuators to apply axial load to the flexible aerodynamic member. The fixture minimizes deflections of a tip of the flexible aerodynamic member during testing to provide an improved accuracy of axial load measurement data.

21 Claims, 13 Drawing Sheets

FIXTURE, SYSTEM, AND METHOD FOR TESTING LOADS IN A FLEXIBLE AERODYNAMIC MEMBER

This invention was made with Government support under W58RGZ-04-G-0023-0267 and W58RGZ-14-D-0075-0042 awarded by The Department of Defense. The government has certain rights in this invention.

BACKGROUND

1) Field of the Disclosure

The disclosure relates generally to fixtures, systems, and methods for load testing of aerodynamic structures, and more particularly, to fixtures, systems, and methods for axial load testing of rotor blades of rotorcraft, such as helicopters.

2) Description of Related Art

Aerodynamic structures, such as rotor blades of rotorcraft, including helicopters or rotary wing aircraft, may be designed, in part, by considering critical loads at limiting flight or ground conditions. Typically, a limiting flight condition is one at which high load factors may be experienced and is one that is usually avoided during normal flight operations. It is desirable that aerodynamic structures, such as rotor blades, be designed with sufficient strength and load-carrying capability to be able to accommodate such high load factors that are experienced at a limiting flight condition, even though such a condition may not be encountered during flight.

Flight test or flight certification or qualification for aerodynamic structures, such as rotor blades of rotorcraft, typically require that such rotor blades undergo and pass testing to verify their load-carrying capability and to confirm the integrity of their design. The rotor blade, or a test specimen representing the rotor blade, may be installed or mounted in a test fixture and subjected to test loads in a controlled environment to simulate loads to which the rotor blade may be subjected when in service. For example, test loads may be applied to the rotor blade, or the test specimen representing the rotor blade, during static and/or fatigue testing to simulate in-flight aerodynamic loads, landing loads, and other loads that may act on the rotor blade during its operational life. However, when test loads, such as axial or centrifugal loads, are applied to the rotor blade, or the test specimen representing the rotor blade, the tip of the rotor blade or test specimen may twist and deflect due to the nature of the shape of the rotor blade or the test specimen, and such twisting and deflection may dilute or change, and in turn, adversely affect, the axial or centrifugal loading characteristics.

Known fixtures, systems, and methods for load testing aerodynamic structures, such as rotor blades, exist. However, such known fixtures, systems, and methods may not be able to adequately control displacement or deflection of the tip of the rotor blade or test specimen during axial or centrifugal load testing, and may result in imprecise or inaccurate axial or centrifugal load test measurements. Moreover, such known fixtures, systems, and methods may not be able to accommodate greater than twelve (12) inches of deflection of the tip of the rotor blade or test specimen during testing, without introducing unwanted loads or moments or other undesirable effects into the rotor blade or test specimen that may not be representative of the actual loads to which the rotor blade may be subjected when in service.

Further, known fixtures, systems, and methods for load testing aerodynamic structures, such as rotor blades, exist that may reduce the displacement or deflection of the tip of the rotor blade or test specimen during axial or centrifugal load testing. However, such known fixtures, systems, and methods may only be used to test very short rotor blades or test specimens, or partial rotor blades, rather than long or full-size rotor blades. The shorter the rotor blade or test specimen, the less area is available for measuring loads during testing. This, in turn, may limit the amount of test data obtained during each test and/or may increase the length and number of tests needed to obtain adequate test data.

In addition, certain rotor blades, depending on the shape of the blade, may require weight pockets disposed within the rotor blade to balance the rotor blade during flight. Such added weight pockets may affect the test results of axial or centrifugal load testing of the rotor blade or test specimen. However, known fixtures, systems, and methods for load testing aerodynamic structures, such as rotor blades, do not provide a solution for handling these weight pockets during axial or centrifugal load testing, so that they do not affect the test results.

Accordingly, there is a need in the art for a fixture, system, and method for testing one or more axial loads in a flexible aerodynamic member, such as a rotor blade, that control and minimize displacement and deflection of the tip of the rotor blade during testing, that allow for precise and accurate axial loading measurements during testing, that enable flight test or flight certification or qualification of the rotor blade, that can successfully be used with rotor blades having weight pockets within the rotor blades, and that provide advantages over known fixtures, systems, and methods.

SUMMARY

Example implementations of this disclosure provide one or more embodiments of a fixture, a system, and a method for testing one or more axial loads in a flexible aerodynamic member, such as rotor blade. As discussed in the below detailed description, embodiments of the fixture, the system, and the method may provide significant advantages over existing fixtures, systems, and methods.

In one exemplary embodiment, there is provided a fixture for testing one or more axial loads in a flexible aerodynamic member. The fixture comprises a structural frame assembly having a first end portion, a second end portion, and an intermediate portion between the first end portion and the second end portion.

The fixture further comprises a first pivotal linkage assembly attached to the first end portion of the structural frame assembly. The first pivotal linkage assembly is pivotable about a pitch axis and is coupled to an axial reaction member. The fixture further comprises a pair of pitch actuators operably coupled to the first pivotal linkage assembly to apply a pitch moment to the first pivotal linkage assembly.

The fixture further comprises a second pivotal linkage assembly attached to the first pivotal linkage assembly. The second pivotal linkage assembly is pivotable about a flap axis. The flap axis is perpendicular to the pitch axis. The second pivotal linkage assembly has a first holding apparatus that holds an inboard end portion of the flexible aerodynamic member. The fixture further comprises a pair of flap actuators operably coupled to the second pivotal linkage assembly to apply a flap bending moment to the second pivotal linkage assembly.

The fixture further comprises a third pivotal linkage assembly attached to the second end portion of the structural frame assembly. The third pivotal linkage assembly is pivotable about the pitch axis, and has a second holding apparatus that holds an outboard end portion of the flexible aerodynamic member. The fixture further comprises a pair of chord actuators operably coupled to the third pivotal linkage assembly to apply an axial load to the flexible aerodynamic member via the third pivotal linkage assembly.

The fixture minimizes deflections of the outboard end portion, or tip, of the flexible aerodynamic member during testing of the one or more axial loads in the flexible aerodynamic member. This provides an improved accuracy of axial load measurement data.

In another exemplary embodiment, there is provided a system for testing one or more axial loads in a flexible aerodynamic member. The system comprises a fixture. The fixture comprises a structural frame assembly having a first end portion, a second end portion, and an intermediate portion between the first end portion and the second end portion.

The fixture further comprises a first pivotal linkage assembly attached to the first end portion. The first pivotal linkage assembly is pivotable about a pitch axis and is coupled to an axial reaction member. The fixture further comprises a pair of pitch actuators operably coupled to the first pivotal linkage assembly, to apply a pitch moment to the first pivotal linkage assembly.

The fixture further comprises a second pivotal linkage assembly attached to the first pivotal linkage assembly. The second pivotal linkage assembly is pivotable about a flap axis. The flap axis is perpendicular to the pitch axis. The fixture further comprises a pair of flap actuators operably coupled to the second pivotal linkage assembly, to apply a flap bending moment to the second pivotal linkage assembly.

The fixture further comprises a third pivotal linkage assembly attached to the second end portion. The third pivotal linkage assembly is pivotable about the pitch axis. The fixture further comprises a pair of chord actuators operably coupled to the third pivotal linkage assembly, to apply an axial load to the flexible aerodynamic member via the third pivotal linkage assembly.

The system further comprises the flexible aerodynamic member having an inboard end portion and an outboard end portion. The flexible aerodynamic member is installed in the fixture, with the inboard end portion mounted to a first holding apparatus of the second pivotal linkage assembly, and with the outboard end portion mounted to a second holding apparatus of the third pivotal linkage assembly.

The system further comprises one or more measuring devices coupled to the flexible aerodynamic member, to measure the one or more axial loads during the testing of the flexible aerodynamic member. The system further comprises a control and data collection system coupled to the fixture to control one or more inputs to the fixture during the testing of the flexible aerodynamic member, and to collect measurement data generated during the testing, including axial load measurement data. The fixture minimizes deflections of the outboard end portion, or tip, of the flexible aerodynamic member during the testing, to provide an improved accuracy of the axial load measurement data.

In another exemplary embodiment, there is provided a method for testing one or more axial loads in a flexible aerodynamic member. The method comprises the step of assembling a fixture for testing one or more axial loads in the flexible aerodynamic member.

The fixture comprises a structural frame assembly having a first end portion, a second end portion, and an intermediate portion between the first end portion and the second end portion. The fixture further comprises a first pivotal linkage assembly attached to the first end portion. The first pivotal linkage assembly is pivotable about a pitch axis and is coupled to an axial reaction member. The fixture further comprises a pair of pitch actuators operably coupled to the first pivotal linkage assembly to apply a pitch moment to the first pivotal linkage assembly.

The fixture further comprises a second pivotal linkage assembly attached to the first pivotal linkage assembly. The second pivotal linkage assembly is pivotable about a flap axis. The flap axis is perpendicular to the pitch axis. The fixture further comprises a pair of flap actuators operably coupled to the second pivotal linkage assembly to apply a flap bending moment to the second pivotal linkage assembly.

The fixture further comprises a third pivotal linkage assembly attached to the second end portion. The third pivotal linkage assembly is pivotable about the pitch axis. The fixture further comprises a pair of chord actuators operably coupled to the third pivotal linkage assembly, to apply an axial load to the flexible aerodynamic member via the third pivotal linkage assembly.

The method further comprises the step of installing the flexible aerodynamic member in the fixture. The flexible aerodynamic member has an inboard end portion and an outboard end portion. The inboard end portion is mounted to a first holding apparatus of the second pivotal linkage assembly. The outboard end portion is mounted to a second holding apparatus of the third pivotal linkage assembly.

The method further comprises the step of controlling one or more inputs to the fixture, with a control and data collection system coupled to the fixture, during the testing of the flexible aerodynamic member. The method further comprises the step of measuring the one or more axial loads in the flexible aerodynamic member, with one or more measuring devices coupled to the flexible aerodynamic member, during the testing of the flexible aerodynamic member.

The method further comprises the step of collecting, with the control and data collection system, measurement data generated during the testing. The fixture minimizes deflections of the outboard end portion, or tip, of the flexible aerodynamic member during the testing to provide an improved accuracy of the measurement data.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

The figures shown in this disclosure represent various aspects of the embodiments presented, and only differences will be discussed in detail.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and fully convey the scope of the disclosure to those skilled in the art.

Figure 1:
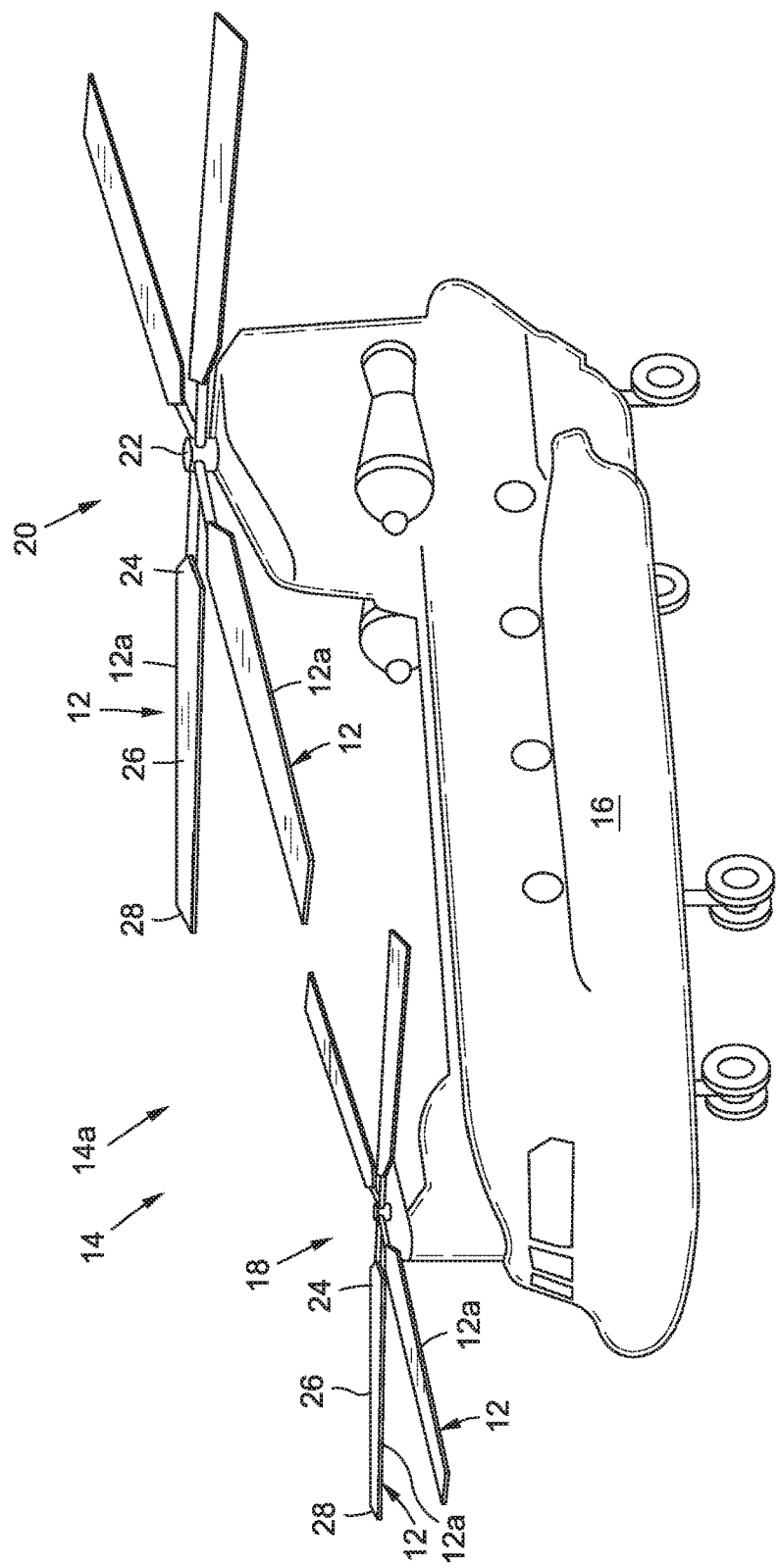
FIG. 1 is an illustration of a perspective view of an air vehicle incorporating a flexible aerodynamic member in the form of a rotor blade that may be tested using one or more embodiments of a fixture, a system, and a method of the disclosure.

Now referring to the Figures, FIG. 1 is an illustration of a perspective view of an air vehicle 14 incorporating a flexible aerodynamic member 12, such as in the form of a rotor blade 12a, that may be tested using one or more embodiments of a fixture 10 (see FIGS. 4B, 5A), a system 300 (see FIGS. 4B, 5A, 8), and a method 400 (see FIG. 9) of the disclosure. As shown in FIG. 1, the air vehicle 14 may be in the form of a rotorcraft 14a, such as a helicopter or rotary wing aircraft, or another suitable air vehicle having a flexible aerodynamic member that may be tested with the fixture 10 (see FIGS. 4B, 5A), the system 300 (see FIGS. 4B, 5A, 8), and/or the method 400 (see FIG. 9) disclosed herein. The flexible aerodynamic member 12 (see FIG. 1) may also comprise aircraft rotor blades, unmanned air vehicle blades, windmill blades, or other suitable flexible aerodynamic members or blades. The flexible aerodynamic member 12, such as in the form of a rotor blade 12a, is preferably made of a composite material, a metal material, or a combination of a composite material and a metal material.

As shown in FIG. 1, the air vehicle 14, such as in the form of the rotorcraft 14a, includes an airframe 16, a forward rotor 18a, an aft rotor 18b, and engines 20. The forward rotor 18a (see FIG. 1) and the aft rotor 18b (see FIG. 1) both include a plurality of flexible aerodynamic members 12 (see FIG. 1), such as in the form of rotor blades 12a (see FIG. 1), and both include a rotor hub 22 (see FIG. 1). As shown in FIG. 1, each of the flexible aerodynamic members 12, such as in the form of rotor blades 12a, includes an inboard end portion 24, an intermediate portion 26, and an outboard end portion 28, or tip. By causing the flexible aerodynamic members 12, such as in the form of rotor blades 12a, to rotate through the atmosphere, lift is produced and the air vehicle 14, such as in the form of rotorcraft 14a, is enabled to fly.

Figure 2:
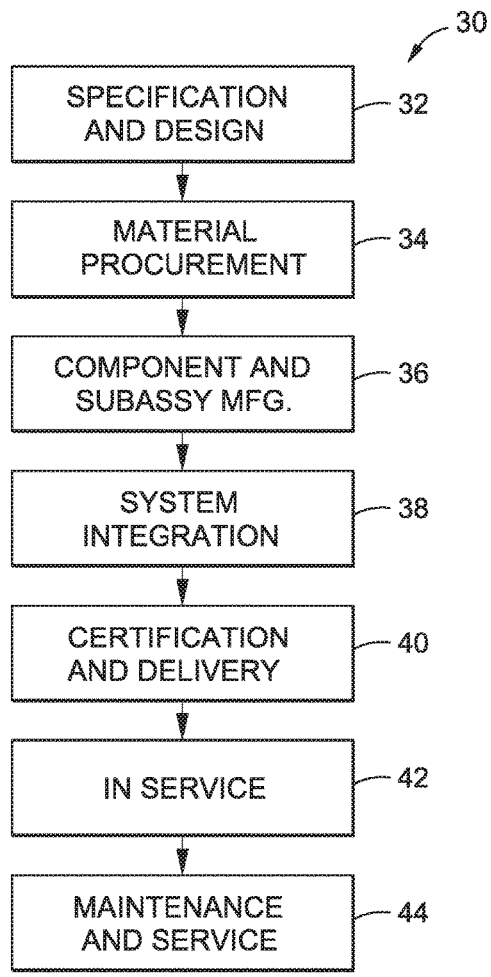
FIG. 2 is a flow diagram of an embodiment of an aircraft manufacturing and service method.
Figure 3:
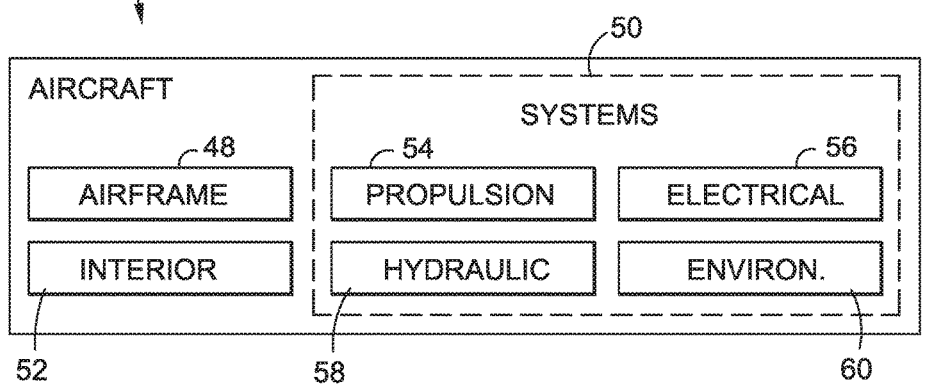
FIG. 3 is an illustration of a functional block diagram of an embodiment of an aircraft.

Now referring to FIGS. 2 and 3, FIG. 2 is a flow diagram of an embodiment of an aircraft manufacturing and service method 30, and FIG. 3 is an illustration of a functional block diagram of an embodiment of an aircraft 46. Referring to FIGS. 2-3, embodiments of the disclosure may be described in the context of the aircraft manufacturing and service method 30, as shown in FIG. 2, and the aircraft 46, as shown in FIG. 3. During pre-production, the exemplary aircraft manufacturing and service method 30 (see FIG. 2) may include specification and design 32 (see FIG. 2) of the aircraft 46 (see FIG. 3) and material procurement 34 (see FIG. 2). During manufacturing, component and subassembly manufacturing 36 (see FIG. 2) and system integration 38 (see FIG. 2) of the aircraft 46 (see FIG. 3) takes place. Thereafter, the aircraft 46 (see FIG. 3) may go through certification and delivery 40 (see FIG. 2) in order to be placed in service 42 (see FIG. 2). While in service 42 (see FIG. 2) by a customer, the aircraft 46 (see FIG. 3) may be scheduled for routine maintenance and service 44 (see FIG. 2), which may also include modification, reconfiguration, refurbishment, and other suitable services.

Each of the processes of the aircraft manufacturing and service method 30 (see FIG. 2) may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may include an airline, leasing company, military entity, service organization, and other suitable operators.

As shown in FIG. 3, the aircraft 46 produced by the exemplary aircraft manufacturing and service method 30 may include an airframe 48 with a plurality of systems 50 and an interior 52. As further shown in FIG. 3, examples of the systems 50 may include one or more of a propulsion system 54, an electrical system 56, a hydraulic system 58, and an environmental system 60. Any number of other systems may be included. Although an aerospace example is shown, the principles of the disclosure may be applied to other industries, such as the automotive industry, including automotive vehicles, the marine industry, including watercraft, ships, and submarines, and other suitable industries.

Methods and systems embodied herein may be employed during any one or more of the stages of the aircraft manufacturing and service method 30 (see FIG. 2). For example, components or subassemblies corresponding to component and subassembly manufacturing 36 (see FIG. 2) may be fabricated or manufactured in a manner similar to components or subassemblies produced while the aircraft 46 (see FIG. 3) is in service 42 (see FIG. 2). Also, one or more method embodiments, system embodiments, or a combination thereof, may be utilized during component and subassembly manufacturing 36 (see FIG. 2) and system integration 38 (see FIG. 2), for example, by substantially expediting assembly of, or reducing the cost of, the aircraft 46 (see FIG. 3). Similarly, one or more of method embodiments, system embodiments, or a combination thereof, may be utilized while the aircraft 46 (see FIG. 3) is in service 42 (see FIG. 2), for example and without limitation, to maintenance and service 44 (see FIG. 2).

Figure 4A:
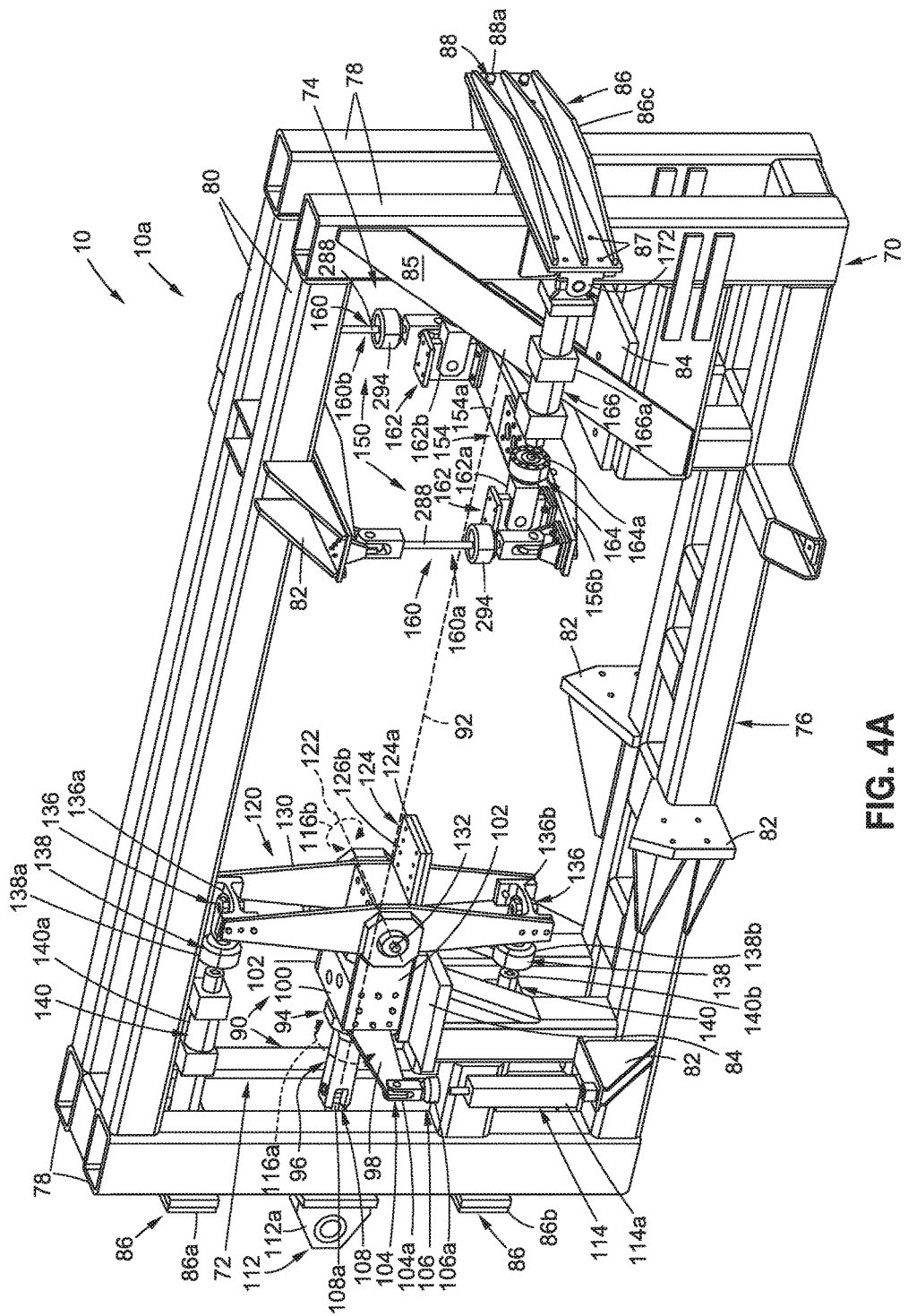
FIG. 4A is an illustration of a front perspective view of an exemplary embodiment of a fixture of the disclosure.
Figure 4B:
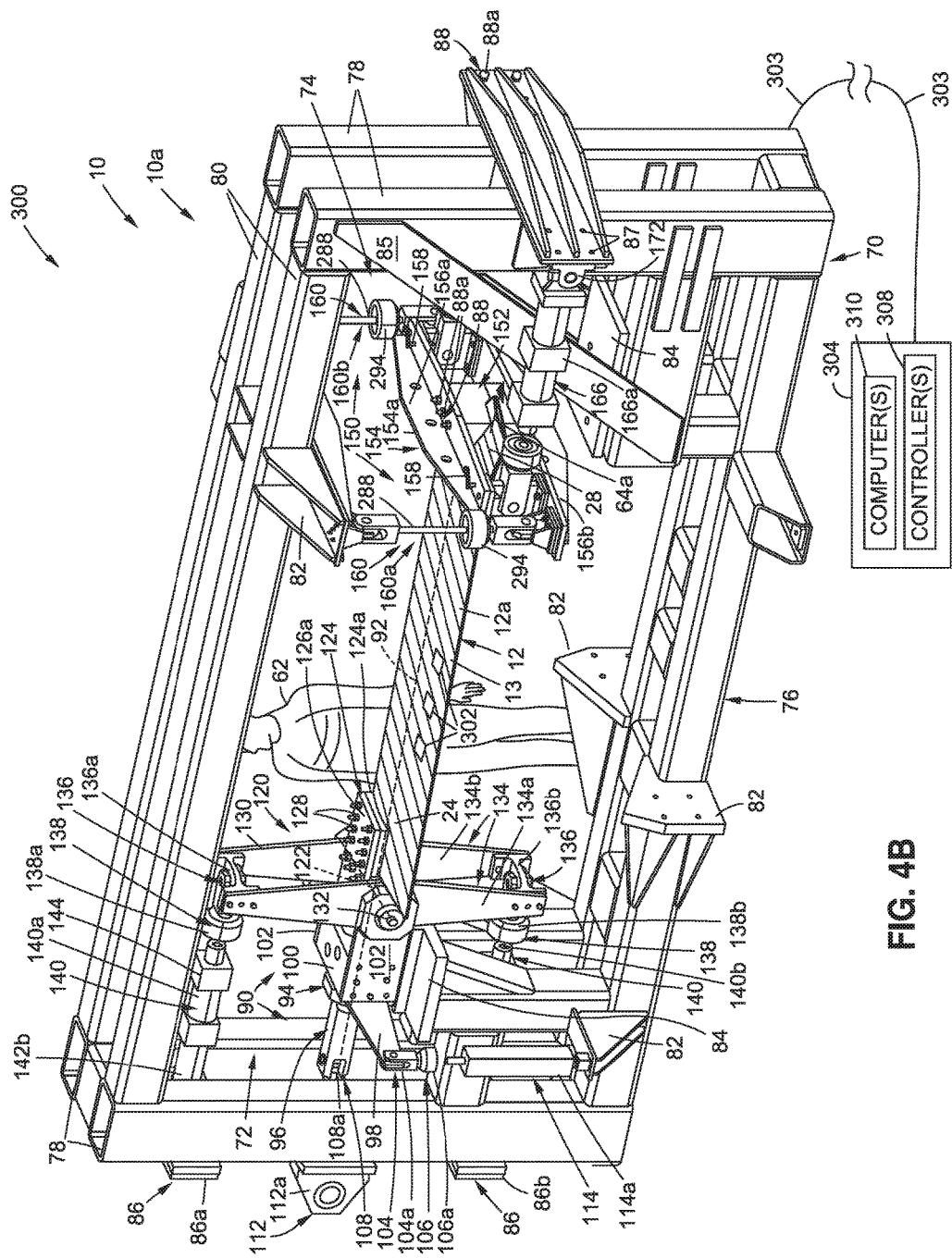
FIG. 4B is an illustration of a front perspective view of the fixture of FIG. 4A showing a flexible aerodynamic member, in the form of a rotor blade, installed in the fixture for testing by a user.

Now referring to FIGS. 4A-4B, FIG. 4A is an illustration of a front perspective view of an exemplary embodiment of a fixture 10, such as in the form of fixture 10a, of the disclosure. FIG. 4B is an illustration of a front perspective view of the fixture 10, such as in the form of fixture 10a, of FIG. 4A, showing a flexible aerodynamic member 12, in the form of a rotor blade 12a, installed in the fixture 10 for testing 63 (see FIG. 8) by a user 62.

Figure 5A:
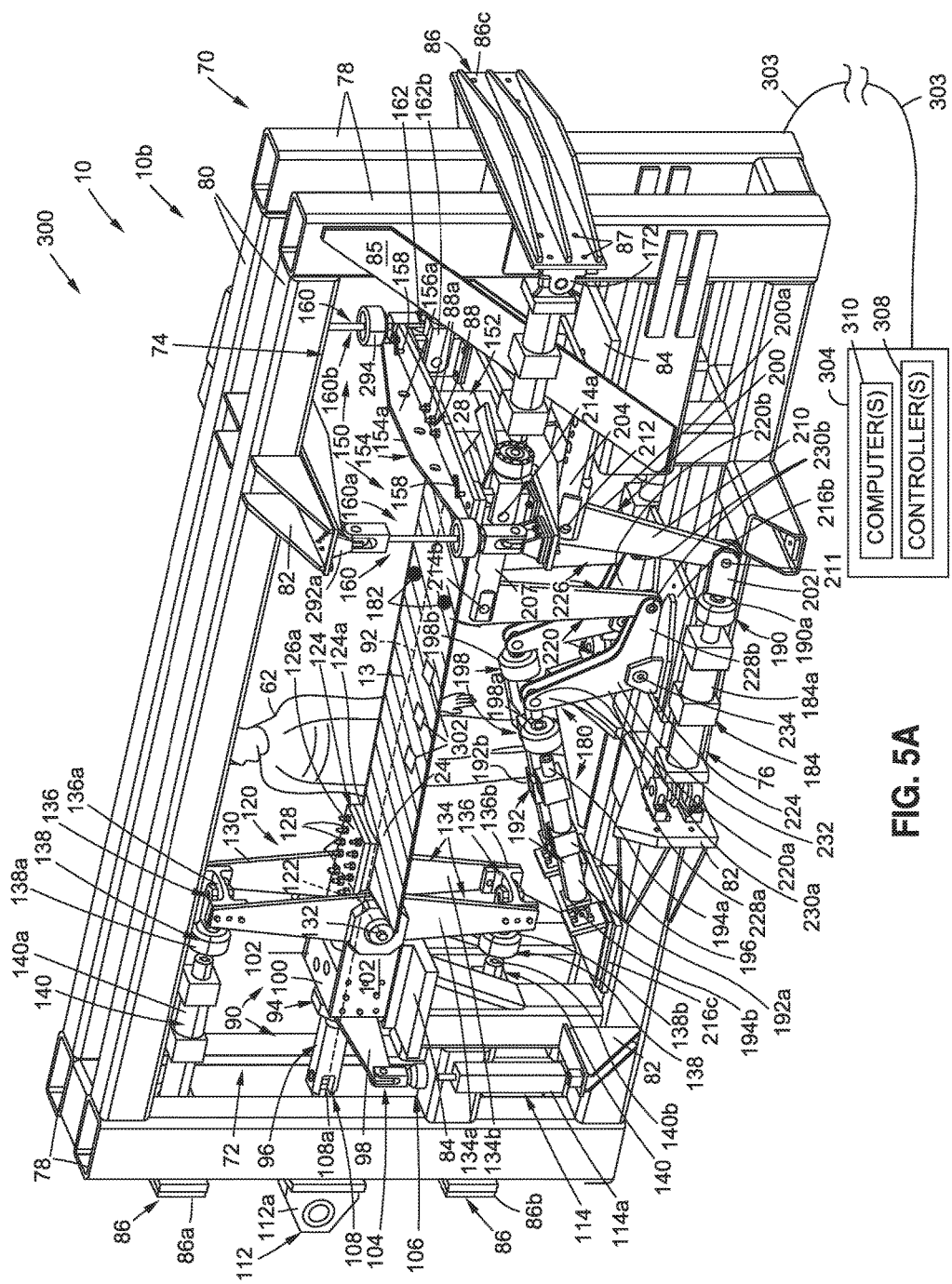
FIG. 5A is an illustration of a front perspective view of another exemplary embodiment of a fixture of the disclosure showing a flexible aerodynamic member, in the form of a rotor blade, installed in the fixture for testing by a user.
Figure 5B:
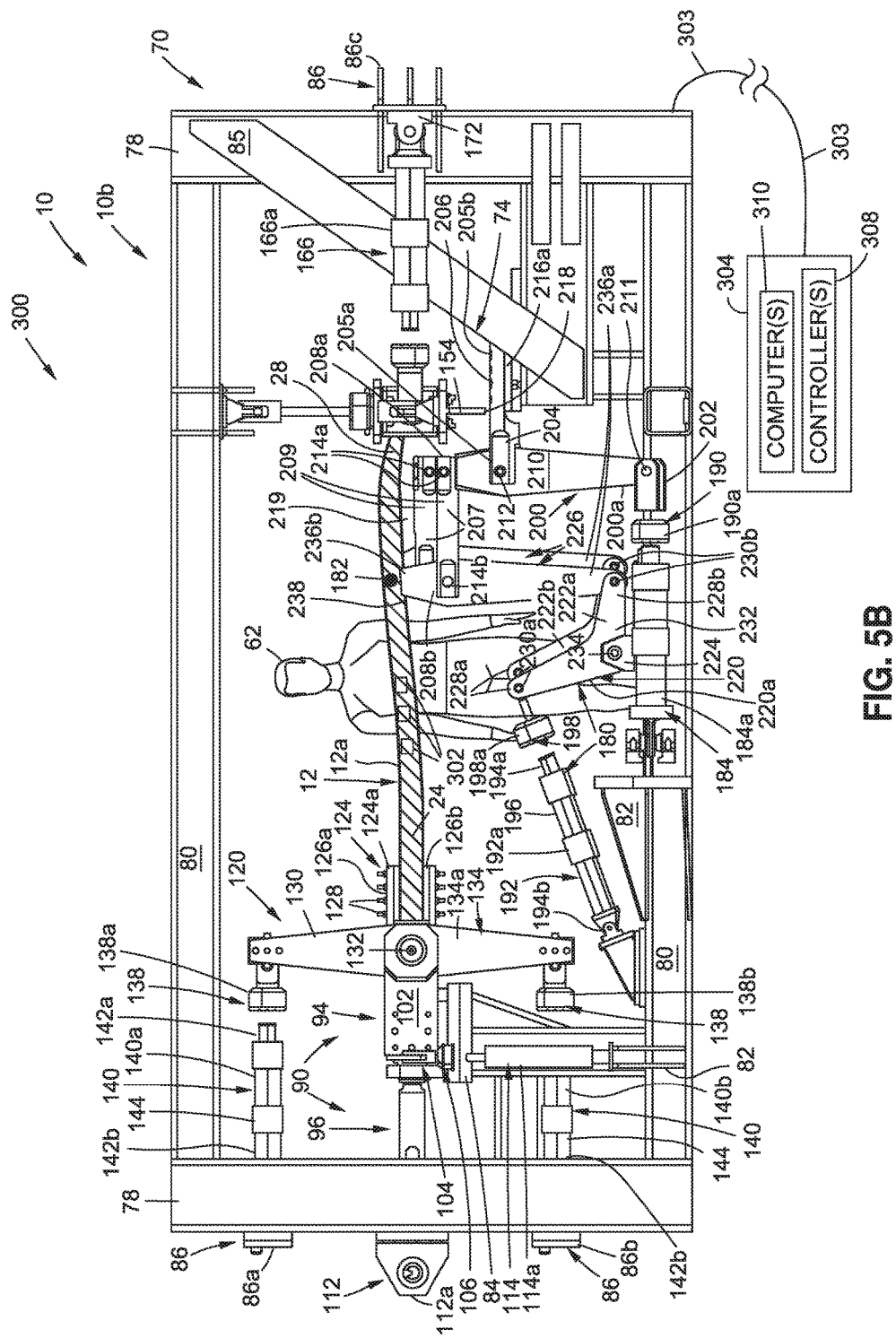
FIG. 5B is an illustration of a front view of the fixture of FIG. 5A with the flexible aerodynamic member, in the form of the rotor blade, installed in the fixture for testing by a user.
Figure 5C:
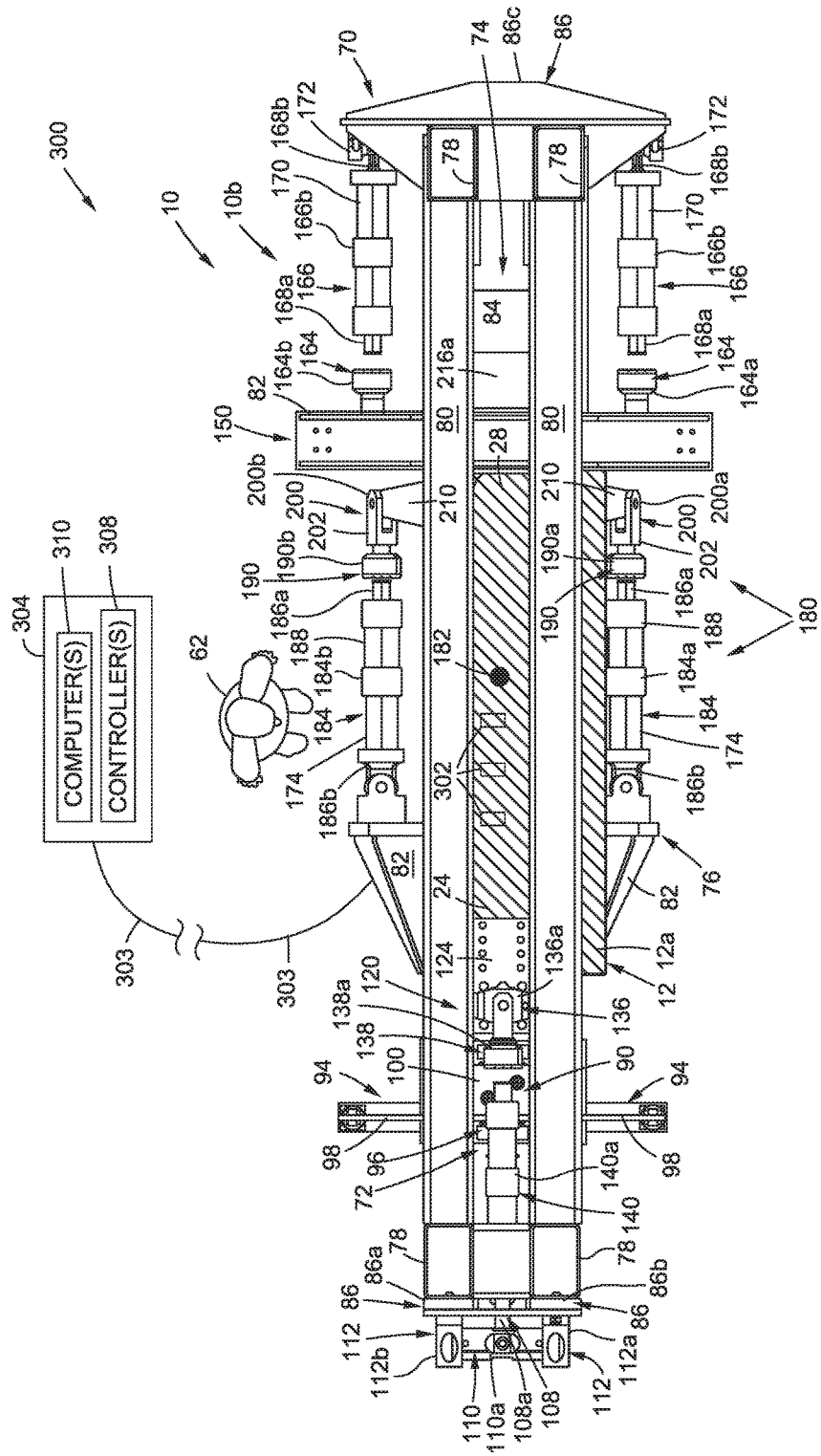
FIG. 5C is an illustration of a top view of the fixture of FIG. 5A with the flexible aerodynamic member, in the form of the rotor blade, installed in the fixture for testing by a user.
Figure 5D:
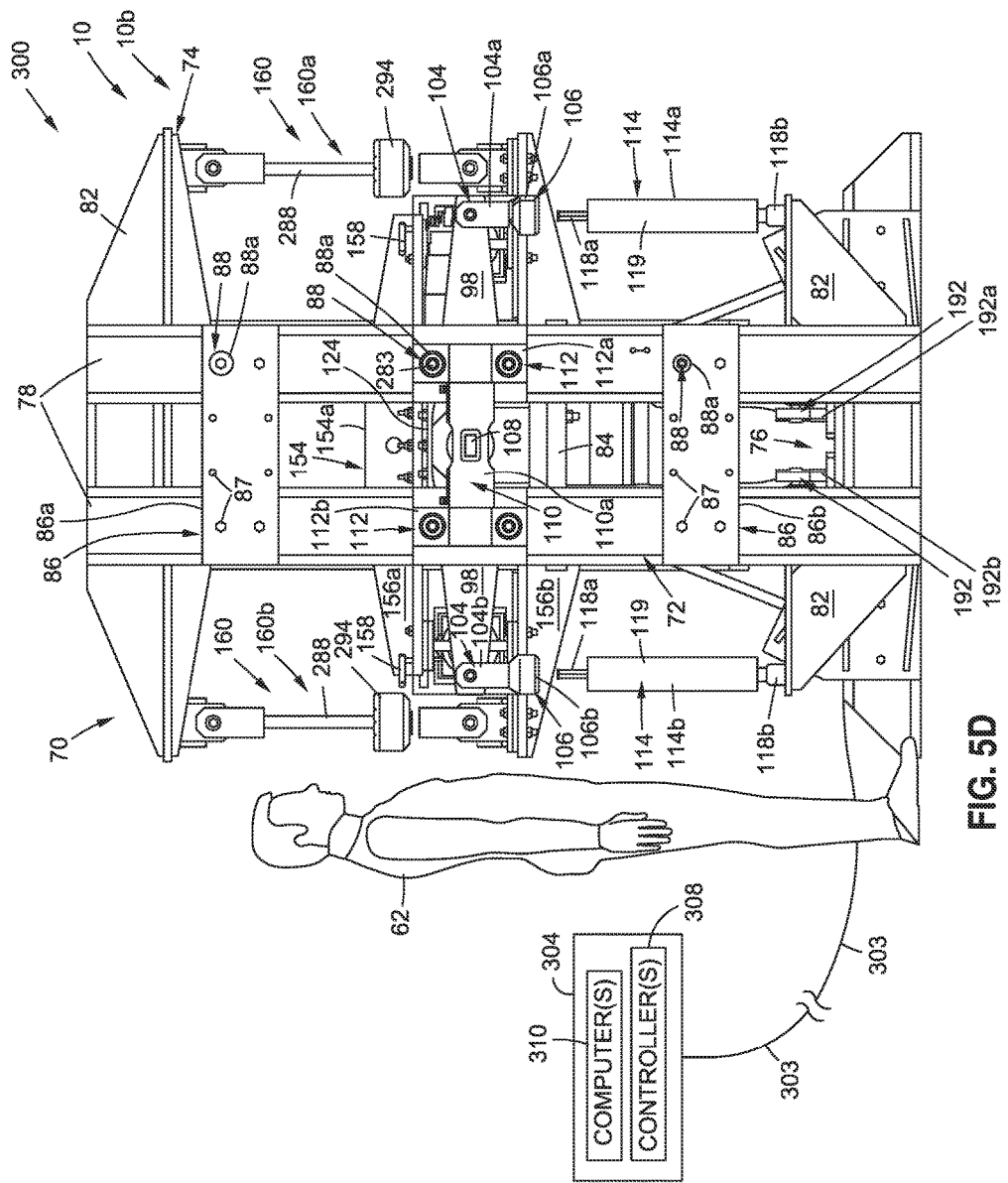
FIG. 5D is an illustration of a right side view of the fixture of FIG. 5A with the flexible aerodynamic member, in the form of the rotor blade, installed in the fixture for testing by a user.

Now referring to FIGS. 5A-5D, FIG. 5A is an illustration of a front perspective view of another exemplary embodiment of a fixture 10, such as in the form of fixture 10b, of the disclosure, showing a flexible aerodynamic member 12, in the form of a rotor blade 12a, installed in the fixture 10, such as in the form of fixture 10b, for testing 63 (see FIG. 8) by a user 62. FIG. 5B is an illustration of a front view of the fixture 10, such as in the form of fixture 10b, of FIG. 5A with the flexible aerodynamic member 12, in the form of the rotor blade 12a, installed in the fixture 10, such as in the form of fixture 10b, for testing 63 (see FIG. 8) by the user 62. FIG. 5C is an illustration of a top view of the fixture, such as in the form of fixture 10b, of FIG. 5A with the flexible aerodynamic member 12, in the form of the rotor blade 12a, installed in the fixture 10, such as in the form of fixture 10b, for testing 63 (see FIG. 8) by the user 62. FIG. 5D is an illustration of a right side view of the fixture, such as in the form of fixture 10b, of FIG. 5A with the flexible aerodynamic member 12, in the form of the rotor blade 12a, installed in the fixture 10, such as in the form of fixture 10b, for testing 63 (see FIG. 8) by the user 62.

The fixture 10 (see FIGS. 4A-5D), such as in the form of fixture 10a (see FIGS. 4A-4B), and in the form of fixture 10b (see FIGS. 5A-5D), is designed for testing 63 (see FIG. 8) one or more loads 64 (see FIG. 8) in the flexible aerodynamic member 12 (see FIGS. 4B, 5A). The flexible aerodynamic member 12 (see FIGS. 4B, 5A) preferably comprises a rotor blade 12a (see FIGS. 4B, 5A) of an air vehicle 14 (see FIG. 1), such as a rotorcraft 14a (see FIG. 1), for example, a helicopter or rotary wing aircraft, or another suitable flexible aerodynamic member or blade. The flexible aerodynamic member 12 (see FIGS. 4B, 5A), such as the rotor blade 12a (see FIGS. 4B, 5A), preferably comprise a test specimen 13 (see FIGS. 4B, 5A) during the testing 63 (see FIG. 8). Preferably, the flexible aerodynamic member 12 (see FIGS. 4B, 5A), such as in the form of rotor blade 12a (see FIGS. 4B, 5A), is cambered and twisted during testing 63 (see FIG. 8) of the one or more loads 64.

The loads 64 (see FIG. 8) may comprise an axial load 64a (see FIG. 8), also referred to as a centrifugal load, a vertical load 64c (see FIG. 8), or another suitable load. The fixture 10 (see FIGS. 4A-5D) minimizes one or more deflections 66 (see FIG. 8) of an outboard end portion 28 (see FIGS. 4B, 5A), or tip, of the flexible aerodynamic member 12 during testing 63 (see FIG. 8) of the one or more loads 64 (see FIG. 8), such as axial loads 64a (see FIG. 8), in the flexible aerodynamic member 12. Minimizing deflections 66 (see FIG. 8) of the tip provides for an improved accuracy 67 (see FIG. 8) of axial load measurement data 68a (see FIG. 8) taken during testing 63 (see FIG. 8). The fixture 10 (see FIGS. 4A-5D) controls the deflections 66 (see FIG. 8) of the outboard end portion 28 (see FIGS. 4B, 5A), or tip, of the flexible aerodynamic member 12 (see FIGS. 4B, 5A) in order to measure the load 64 (see FIG. 8), such as axial load 64a (see FIG. 8), of the flexible aerodynamic member 12 that may deflect based on the shape of the flexible aerodynamic member 12.

As shown in FIGS. 4A-5D, the fixture 10, such as in the form of fixture 10a (see FIG. 4A) and fixture 10b (see FIG. 5A), comprises a structural frame assembly 70 comprising a first end portion 72, a second end portion 74, and an intermediate portion 76 positioned between the first end portion 72 and the second end portion 74. As further shown in FIGS. 4A-5D, the structural frame assembly 70 preferably comprises a plurality of vertical frame beams 78, and a plurality of horizontal frame beams 80 perpendicular to the plurality of vertical frame beams 78. As further shown in FIGS. 4A-5D, the structural frame assembly 70 comprises a plurality of cross support structures 82 attached to one or more of the plurality of vertical frame beams 78 and to one or more of the plurality of horizontal frame beams 80 to provide added support and stability to the structural frame assembly 70. As further shown in FIGS. 4A-5D, the structural frame assembly 70 comprises a plurality of platform assemblies 84 assembled at the first end portion 72, at the second end portion 74, and/or at the intermediate portion 76 for supporting various parts of the fixture 10.

The structural frame assembly 70 (see FIGS. 4A-5B) further comprises a diagonal brace 85 (see FIGS. 4A-5B) attached at the second end portion 74 (see FIGS. 4A-5B). The diagonal brace 85 (see FIGS. 4A-5B) provides added support and reduces the stresses of loading at the second end portion 74 (see FIGS. 4A-5B).

The structural frame assembly 70 (see FIGS. 4A-5D) further comprises a plurality of actuator reaction plates 86 (see FIGS. 4A-5D). The plurality of actuator reaction plates 86 (see FIGS. 4A-5D) may comprise an upper flap actuator reaction plate 86a (see FIGS. 4A-5D) and a lower flap actuator reaction plate 86b (see FIGS. 4A-5B, 5D) attached at the first end portion 72 (see FIGS. 4A-5D), may comprise a chord actuator reaction plate 86c (see FIGS. 4A-5C) attached at the second end portion 74 (see FIGS. 4A-5C), or may comprise another suitable actuator reaction plate 86. The plurality of actuator reaction plates 86 (see FIGS. 4A, 5A, 5D), such as in the form of the upper flap actuator reaction plate 86a (see FIG. 5D), the lower flap actuator reaction plate 86b (see FIG. 5D), and the chord actuator reaction plate 86c (see FIGS. 4A, 5A), may each comprise a plurality of actuator reaction plate holes 87 (see FIGS. 4A, 5A, 5D). Each actuator reaction plate hole 87 (see FIGS. 4A, 5A, 5D) is configured to receive an attachment element 88 (see FIGS. 4A, 5A, 5D). The attachment element 88 (see FIGS. 4A, 5A, 5D, 8) may be in the form of a bolt 88a (see FIGS. 4A, 5A, 5D, 8), a pin 88b (see FIG. 8), a dowel 88c (see FIG. 8), a screw 88d (see FIGS. 6A, 8), a fastener 88e (see FIG. 8), or another suitable attachment element 88.

The structural frame assembly 70 (see FIGS. 4A-5D) is preferably constructed of a strong and sturdy material, such as a strong and sturdy metal material, for example, steel. The parts of the structural frame assembly 70 (see FIGS. 4A-5D)

may be welded or soldered together, may be attached together with a plurality of attachment elements 88 (see FIG. 8), or a combination thereof.

As shown in FIGS. 4A-5D, the fixture 10, such as in the form of fixture 10a (see FIG. 4A) and fixture 10b (see FIG. 5A), further comprises a first pivotal linkage assembly 90 attached to the first end portion 72 of the structural frame assembly 70. The first pivotal linkage assembly 90 (see FIGS. 4A-5D) is pivotable about a pitch axis 92 (see FIGS. 4B, 5A, 6A-6B).

As further shown in FIGS. 4A-5C, the first pivotal linkage assembly 90 comprises a first pivot arm assembly 94 pivotally coupled to a first pin joint 96. As further shown in FIGS. 4A-5B, the first pivot arm assembly 94 comprises a horizontal arm 98, a first pin joint link 100 attached to the horizontal arm 98, and a pair of side plates 102 attached to the first pin joint link 100.

As further shown in FIGS. 4A-5B, 5D, the horizontal arm 98 is coupled to a pair of pitch actuator lugs 104, and the pair of pitch actuator lugs 104 is coupled to a pair of pitch actuator load cells 106, respectively. The pair of pitch actuator lugs 104 (see FIGS. 4A, 5D) preferably comprise a first pitch actuator lug 104a (see FIGS. 4A, 5D) and a second pitch actuator lug 104b (see FIG. 5D). The pair of pitch actuator load cells 106 (see FIGS. 4A, 5D) preferably comprise a first pitch actuator load cell 106a (see FIGS. 4A, 5D) and a second pitch actuator load cell 106b (see FIG. 5D).

The first pin joint 96 (see FIGS. 4A-5C) of the first pivotal linkage assembly 90 (see FIGS. 4A-5C) is preferably coupled to an axial reaction member 108 (see FIGS. 4A-5C), such as in the form of a tie bar 108a (see FIGS. 4A-5C), or another suitable bar or elongated structure. The axial reaction member 108 (see FIGS. 5C-5D) is coupled to a pin 110 (see FIGS. 5C-5D), such as in the form of a trunnion pin 110a (see FIGS. 5C-5D). The pin 110 (see FIGS. 5C-5D) may be attached to a pair of couplings 112 (see FIGS. 4A-5D), such as in the form of a first coupling 112a (see FIGS. 4A-5D) and a second coupling 112b (see FIGS. 5C-5D).

The first pivotal linkage assembly 90 (see FIGS. 4A-5D) is preferably constructed of strong and sturdy materials, such as a strong and sturdy metal material, for example, steel, and/or a strong and sturdy plastic material. The parts of the first pivotal linkage assembly 90 (see FIGS. 4A-5D) may be welded or soldered together, may be attached together with a plurality of attachment elements 88 (see FIG. 8), or a combination thereof. The first pivotal linkage assembly 90 (see FIGS. 4A-5D) is discussed in further detail below with respect to FIGS. 6A-6B.

As shown in FIGS. 4A-5B and 5D, the fixture 10, such as in the form of fixture 10a (see FIG. 4A), and fixture 10b (see FIG. 5A), further comprises a pair of pitch actuators 114, operably coupled to the first pivot arm assembly 94 of the first pivotal linkage assembly 90, to apply a moment 116 (see FIG. 8), such as in the form of a pitch moment 116a (see FIGS. 4A, 8), to the first pivot arm assembly 94 of the first pivotal linkage assembly 90. As shown in FIG. 5D, the pair of pitch actuators 114 preferably comprises a first pitch actuator 114a and a second pitch actuator 114b. The first pitch actuator 114a (see FIG. 5D) and the second pitch actuator 114b (see FIG. 5D) each has an upper end 118a (see FIG. 5D), a lower end 118b (see FIG. 5D), and a body 119 (see FIG. 5D) formed between the upper end 118a and the lower end 118b. As further shown in FIG. 5D, the upper end 118a of each of the first and second pitch actuators 114a, 114b, is configured to couple to, and during testing 63 (see FIG. 8), is operably coupled to, the first pitch actuator load cell 106a and the second pitch actuator load cell 106b, respectively. As further shown in FIG. 5D, the lower end 118b of each of the first and second pitch actuators 114a, 114b, is attached to cross support structures 82.

As shown in FIGS. 4A-5C, the fixture 10, such as in the form of fixture 10a (see FIG. 4A), and fixture 10b (see FIG. 5A), further comprises a second pivotal linkage assembly 120 attached to the first pivotal linkage assembly 90. The second pivotal linkage assembly 120 (see FIGS. 4A-5C) is pivotable about a flap axis 122 (see FIGS. 4B, 5A, 6A-6B). The flap axis 122 (see FIGS. 4B, 5A, 6A-6B) is perpendicular, or orthogonal, to the pitch axis 92 (see FIGS. 4B, 5A, 6A-6B).

The second pivotal linkage assembly 120 (see FIGS. 4A-5C) further has a first holding apparatus 124 (see FIGS. 4A-5D) that is configured to hold, and during testing 63 (see FIG. 8), holds an inboard end portion 24 (see FIGS. 4B-5C) of the flexible aerodynamic member 12 (see FIGS. 4B-5C), such as the rotor blade 12a (see FIGS. 4B-5C). The first holding apparatus 124 (see FIGS. 4B, 5A-5B) may preferably be in the form of a clamp plate apparatus 124a (see FIGS. 4B, 5A-5B) having one or more upper clamp plates 126a (see FIGS. 4B, 5A-5B) and one or more lower clamp plates 126b (see FIGS. 4A, 5B) that may be secured together via clamp plate attachments 128 (see FIGS. 4B, 5A-5B).

As shown in FIGS. 4A-5B, the second pivotal linkage assembly 120 comprises a second pivot arm assembly 130 pivotally coupled to a second pin joint 132. As further shown in FIGS. 4A-5B, the second pivot arm assembly 130 comprises a pair of vertical arms 134 each attached via the second pin joint 132 to the first pivot arm assembly 94 of the first pivotal linkage assembly 90.

As further shown in FIGS. 4A-5A, a pair of flap link assemblies 136 comprising an upper flap link assembly 136a and a lower flap link assembly 136b, are preferably attached to the pair of vertical arms 134. A pair of flap actuator load cells 138 (see FIGS. 4A-5C) are preferably coupled to the pair of flap link assemblies 136 (see FIGS. 4A-5C), respectively. The pair of flap actuator load cells 138 (see FIGS. 4A-5C) comprise an upper flap actuator load cell 138a (see FIGS. 4A-5C) and a lower flap actuator load cell 138b (see FIGS. 4A-5B), where the upper flap actuator load cell 138a is attached to the upper flap link assembly 136a, and the lower flap actuator load cell 138b is attached to the lower flap link assembly 136b. The second pivotal linkage assembly 120 (see FIGS. 4A-5D) is discussed in further detail below with respect to FIGS. 6A-6B.

As shown in FIGS. 4A-5B, the fixture 10, such as in the form of fixture 10a (see FIG. 4A), and fixture 10b (see FIG. 5A), further comprises a pair of flap actuators 140 operably coupled to the second pivot arm assembly 130 of the second pivotal linkage assembly 120. The pair of flap actuators 140 (see FIGS. 4A-5C) comprise an upper flap actuator 140a (see FIGS. 4A-5C) and a lower flap actuator 140b (see FIGS. 4A-5B). The upper flap actuator 140a (see FIGS. 4B, 5B) and the lower flap actuator 140b (see FIGS. 4B, 5B) each has a first end 142a (see FIGS. 4B, 5B), a second end 142b (see FIGS. 4B, 5B), and a body 144 (see FIGS. 4B, 5B) formed between the first end 142a and the second end 142b. As further shown in FIG. 5B, the first end 142a of each of the upper and lower flap actuators 140a, 140b, is configured to couple to, and during testing 63 (see FIG. 8), is operably coupled to, the upper flap actuator load cell 138a and the lower flap actuator load cell 138b, respectively. As further shown in FIG. 5B, the second end 142b of each of the upper and lower flap actuators 140a, 140b, is attached to the upper flap actuator reaction plate 86*a* and to the lower flap actuator reaction plate 86*b*, respectively.

The pair of flap actuators 140 (see FIGS. 4A-5B) function as moment balancing members 146 (see FIGS. 6A, 8) and are configured to apply a moment 116 (see FIG. 8), such as in the form of a flap bending moment 116*b* (see FIGS. 4A, 8), to the second pivot arm assembly 130 (see FIGS. 4A-4B) of the second pivotal linkage assembly 120. In addition, the second pivot arm assembly 130 (see FIGS. 4A-4B) applies a balancing force 148 (see FIG. 8) to balance the moment 116 (see FIG. 8) induced on the flexible aerodynamic member 12 (see FIGS. 4B, 5A), such as the rotor blade 12*a* (see FIGS. 4B, 5A), by a third pivotal linkage assembly 150 (see FIGS. 4A-5D).

As shown in FIGS. 4A-5D, the fixture 10, such as in the form of fixture 10*a* (see FIG. 4A), and fixture 10*b* (see FIG. 5A), further comprises the third pivotal linkage assembly 150 attached to the second end portion 74 of the structural frame assembly 70. The third pivotal linkage assembly 150 (FIGS. 4B-5B) is pivotable about the pitch axis 92 (FIGS. 4B, 5A, 6A-6B, 7), and has a second holding apparatus 152 (FIGS. 4B-5B) that holds the outboard end portion 28 (FIGS. 4B-5B), or tip, of the flexible aerodynamic member 12 (FIGS. 4B-5B), such as the rotor blade 12*a* (see FIGS. 4B-5B). The third pivotal linkage assembly 150 (FIGS. 4A-5A, 5D) comprises a mounting assembly 154 (see FIGS. 4A-5B, 5D). Preferably, the mounting assembly 154 (see FIGS. 4A-5B, 5D) is in the form of a weldment assembly 154*a* (see FIGS. 4A-5B, 5D), or another suitable mounting assembly 154.

The mounting assembly 154 (see FIGS. 4A-5B, 5D) comprises a removable upper piece 156*a* (see FIGS. 4B-5B, 5D) and a fixed lower piece 156*b* (see FIGS. 4A-5B, 5D). The mounting assembly 154 (see FIGS. 4B-5A, 5D) further comprises a plurality of alignment pins 158 (see FIGS. 4B-5A, 5D) removably attached to the removable upper piece 156*a* (see FIGS. 4B-5A, 5D) for alignment of the removable upper piece 156*a* with the fixed lower piece 156*b* (see FIGS. 4B-5A, 5D). The mounting assembly 154 (see FIGS. 4B-5A) further comprises a plurality of attachment elements 88 (see FIGS. 4B-5A), such as in the form of bolts 88*a* (see FIGS. 4B-5A), or another suitable attachment element 88, to attach the removable upper piece 156*a* (see FIGS. 4B-5A) to the second holding apparatus 152 (see FIGS. 4B-5A), which is attached between the removable upper piece 156*a* and the fixed lower piece 156*b* (see FIGS. 4B-5A) of the mounting assembly 154.

The third pivotal linkage assembly 150 (see FIGS. 4A-5B, 5D) further comprises a pair of flap reaction link assemblies 160 (see FIGS. 4A-5B, 5D) attached to the mounting assembly 154 (see FIGS. 4A-5B, 5D). The pair of flap reaction link assemblies 160 (see FIGS. 4A, 5A, 5D) preferably comprise a first flap reaction link assembly 160*a* (see FIGS. 4A, 5A, 5D) and a second flap reaction link assembly 160*b* (see FIGS. 4A, 5A, 5D) positioned opposite the first flap reaction link assembly 160*a*.

The third pivotal linkage assembly 150 (see FIGS. 4A, 5A) further comprises a pair of chord actuator lug assemblies 162 (see FIGS. 4A, 5A) attached to the mounting assembly 154 (see FIGS. 4A, 5A). The pair of chord actuator lug assemblies 162 (see FIGS. 4A, 5A) preferably comprise a first chord actuator lug assembly 162*a* (see FIGS. 4A, 5A) and a second chord actuator lug assembly 162*b* (see FIGS. 4A, 5A) positioned opposite the first chord actuator lug assembly 164*a*. As shown in FIGS. 4A, 5D, and as discussed in further detail below with respect to FIG. 7, the chord actuator lug assemblies 162 comprise flap reaction links 288 and flap reaction link load cells 294.

The third pivotal linkage assembly 150 (see FIGS. 4A, 5C) further comprises a pair of chord actuator load cells 164 (see FIGS. 4A, 5C) coupled to the pair of chord actuator lug assemblies 162 (see FIGS. 4A, 5A), respectively. The pair of chord actuator load cells 164 (see FIGS. 4A, 5C) preferably comprise a first chord actuator load cell 164*a* (see FIGS. 4A, 5C, 7) and a second chord actuator load cell 164*b* (see FIGS. 5C, 7) positioned opposite the first chord actuator load cell 164*a*.

The third pivotal linkage assembly 150 (see FIGS. 4A-5D) is discussed in further detail below with respect to FIG. 7.

As shown in FIGS. 4A-5C, the fixture 10, such as in the form of fixture 10*a* (see FIG. 4A), and fixture 10*b* (see FIG. 5A), further comprises a pair of chord actuators 166 operably coupled to the third pivotal linkage assembly 150, to apply an axial load 64*a* (see FIGS. 4B, 8) to the flexible aerodynamic member 12 (see FIGS. 4B, 5A), via the third pivotal linkage assembly 150. The pair of chord actuators 166 (see FIGS. 4A-5C) preferably comprises a first chord actuator 166*a* (see FIGS. 4A-5C) and a second chord actuator 166*b* (see FIG. 5C). As shown in FIG. 5C, the first chord actuator 166*a* and the second chord actuator 166*b* each has a first end, a second end 168*b*, and a body 170 formed between the first end 168*a* and the second end 168*b*.

As further shown in FIG. 5C, the first end 168*a* of each of the first and second chord actuators 166*a*, 166*b*, is configured to couple to, and during testing 63 (see FIG. 8), is operably coupled to, the first chord actuator load cell 164*a* and the second chord actuator load cell 164*b*, respectively. The second end 168*b* (see FIGS. 4A-4B, 5C) of each of the first and second chord actuators 166*a*, 166*b* (see FIG. 5C), is attached to an actuator reaction plate 86, such as the chord actuator reaction plate 86*c* (see FIGS. 4A-4B, 5C), via bracket attachments 172 (see FIGS. 4A-4B, 5C).

The pair of chord actuators 166 (see FIGS. 4A, 5B, 5C) function as axial loading members 174 (see FIGS. 7, 8) and are configured to apply axial load 64*a* (see FIGS. 4B, 8) to the flexible aerodynamic member 12 (see FIGS. 4B, 5A), via the third pivotal linkage assembly 150, to enable a distributed load 64*b* (see FIG. 8) on the outboard end portion 28 (see FIGS. 4B, 5A), or tip, of the flexible aerodynamic member 12 (see FIGS. 4B, 5A), such as the rotor blade 12*a* (see FIGS. 4B, 5A). In addition, the pair of flap reaction link assemblies 160 (see FIGS. 4A-5B, 5D) function as torsional reaction members 176 (see FIGS. 7, 8) configured to react a torsional reaction 178 (see FIG. 8) of the outboard end portion 28 (see FIGS. 4B, 5A), or tip, of the flexible aerodynamic member 12 (see FIGS. 4B, 5A), such as the rotor blade 12*a* (see FIGS. 4B, 5A), when the pair of chord actuators 166 (see FIGS. 4A, 5B, 5C) apply the axial load 64*a* (see FIGS. 4B, 8) to the flexible aerodynamic member 12 (see FIGS. 4B, 5A).

In another embodiment, as shown in FIGS. 5A-5D, the fixture 10, such as in the form of fixture 10*b*, may further comprise a fourth pivotal linkage assembly 180 attached substantially to the intermediate portion 76 of the structural frame assembly 70. The fourth pivotal linkage assembly 180 (see FIGS. 5A-5D) is positioned underneath, or substantially underneath, the flexible aerodynamic member 12 (see FIGS. 5A-5D), such as the rotor blade 12*a* (see FIGS. 5A-5D), when the flexible aerodynamic member 12, such as the rotor blade 12*a*, is mounted to and positioned between the first holding apparatus 124 (see FIGS. 5A-5D) and the second holding apparatus 152 (see FIGS. 5A-5B), and when the flexible aerodynamic member 12, such as the rotor blade 12a, has one or more load distribution weighted elements 182 (see FIGS. 5A-5C), or weight pockets, disposed within the flexible aerodynamic member 12, such as the rotor blade 12a.

Such load distribution weighted elements 182 (see FIGS. 5A-5C, 8), or weight pockets, may be required in certain rotor blades, depending on the shape of the blade, to balance the rotor blade during flight. The one or more load distribution weighted elements 182 (see FIGS. 5A-5C), or weight pockets, preferably each comprise a metal element or structure, such as made of steel, that is bonded or attached within the flexible aerodynamic member 12, such as the rotor blade 12a. The one or more load distribution weighted elements 182 (see FIGS. 5A-5C) provide a weight pocket or a balanced weight within one or more portions of the flexible aerodynamic member 12, such as the rotor blade 12a, during testing 63 (see FIG. 8), such as load testing, of the flexible aerodynamic member 12, such as the rotor blade 12a. The use of the fixture 10b (see FIGS. 5A-5D) with the attached fourth pivotal linkage assembly 180 (see FIGS. 5A-5D) for testing of the rotor blade 12a (see FIGS. 5A-5B) with the one or more load distribution weighted elements 182 (see FIGS. 5A-5C) within the rotor blade 12a results in minimal deflections 66 (see FIG. 8) of the outboard end portion 28 (see FIGS. 5A-5B), or tip, of the rotor blade 12a, and provides improved accuracy 67 (see FIG. 8) and precision of measurement data 68 (see FIG. 8), such as axial load measurement data 68a (see FIG. 8), or other relevant data, obtained during testing.

As shown in FIGS. 5A-5C, the fourth pivotal linkage assembly 180 comprises a pair of axial actuators 184. The pair of axial actuators (see FIGS. 5A-5C) preferably comprise a first axial actuator 184a (see FIGS. 5A-5C) and a second axial actuator 184b (see FIGS. 5A, 5C). As shown in FIG. 5C, the first axial actuator 184a and the second axial actuator 184b each has a first end 186a, a second end 186b, and a body 188 formed between the first end 186a and the second end 186b.

The fourth pivotal linkage assembly 180 (see FIGS. 5A-5C) further comprises a pair of axial actuator load cells 190 (see FIGS. 5A-5C). The pair of axial actuator load cells 190 (see FIGS. 5A-5C) preferably comprise a first axial actuator load cell 190a (see FIGS. 5A-5C) and a second axial actuator load cell 190b (see FIG. 5C). As shown in FIG. 5C, the first end 186a of the first axial actuator 184a is configured to couple to, and during testing 63 (see FIG. 8), is operably coupled to, the first axial actuator load cell 190a, and the first end 186a of the second axial actuator 184b is configured to couple to, and during testing 63 (see FIG. 8), is operably coupled to, the second axial actuator load cell 190b. The second end 186b (see FIG. 5C) of the first axial actuator 184a (see FIG. 5C) and the second end 186b (see FIG. 5C) of the second axial actuator 186b (see FIG. 5C) are preferably each attached to cross support structures 82 (see FIG. 5C).

As shown in FIGS. 5A-5B, 5D, the fourth pivotal linkage assembly 180 further comprises a pair of vertical actuators 192. The pair of vertical actuators 192 (see FIGS. 5A-5B, 5D) preferably comprise a first vertical actuator 192a (see FIGS. 5A-5B, 5D) and a second vertical actuator 192b (see FIGS. 5A-5B, 5D). The first vertical actuator 192a (see FIGS. 5A-5B) and the second vertical actuator 192b (see FIG. 5A) each has a first end 194a (see FIGS. 5A-5B), a second end 194b (see FIGS. 5A-5B), and a body 196 (see FIGS. 5A-5B) formed between the first end 194a and the second end 194b.

The fourth pivotal linkage assembly 180 (see FIGS. 5A-5B) further comprises a pair of vertical actuator load cells 198 (see FIGS. 5A-5B). The pair of vertical actuator load cells 198 (see FIGS. 5A-5B) preferably comprise a first vertical actuator load cell 198a (see FIGS. 5A-5B) and a second vertical actuator load cell 198b (see FIG. 5A). As shown in FIG. 5A, the first end 194a of the first vertical actuator 192a is configured to couple to, and during testing 63 (see FIG. 8), is operably coupled to, the first vertical actuator load cell 198a, and the first end 194a of the second vertical actuator 192b is configured to couple to, and during testing 63 (see FIG. 8), is operably coupled to, the second vertical actuator load cell 198b. The second end 194b (see FIG. 5A) of the first vertical actuator 192a (see FIG. 5A) and the second end 194b (see FIG. 5A) of the second vertical actuator 192b (see FIG. 5A) are preferably each attached to a fixed platform structure 216c (see FIG. 5A), which is, in turn, attached to horizontal frame beams 80 (see FIG. 5A).

As shown in FIGS. 5A-5C, the fourth pivotal linkage assembly 180 further comprises a pair of axial actuator link assemblies 200 (configured for actuation by the pair of axial actuators 184. The pair of axial actuator link assemblies 200 (see FIGS. 5A-5C) comprise a first axial actuator link assembly 200a (see FIGS. 5A-5C) and a second axial actuator link assembly 200b (see FIG. 5C) opposite the first axial actuator link assembly 200a. The first and second axial actuator link assemblies 200a, 200b (see FIGS. 5A-5C) preferably each comprises a lug member 202 (see FIGS. 5A-5C) coupled to an axial actuator load cell 190 (see FIGS. 5A-5C).

The first and second axial actuator link assemblies 200a, 200b (see FIGS. 5A-5C) preferably each further comprises a first connector portion 204 (see FIGS. 5A-5B) with a first end 205a (see FIG. 5B), a second end 205b (see FIG. 5B), and a body 206 (see FIG. 5B). The first and second axial actuator link assemblies 200a, 200b (see FIGS. 5A-5C) preferably each further comprises a second connector portion 207 (see FIGS. 5A-5B) with a first end 208a (see FIG. 5B), a second end 208b (see FIG. 5B), and a body 209 (see FIG. 5B).

The first and second axial actuator link assemblies 200a, 200b (see FIGS. 5A-5C) preferably each further comprises an axial actuator arm 210 (see FIGS. 5A-5C). Each axial actuator arm 210 (see FIGS. 5A-5B) is preferably pivotally attached to the lug member 202 (see FIGS. 5A-5B) via a pin element 211 (see FIGS. 5A-5B). Each axial actuator arm 210 (see FIGS. 5A-5B) is preferably attached to the first connector portion 204 (see FIGS. 5A-5B) via a first connector element 212 (see FIGS. 5A-5B), and is preferably attached to the second connector portion 207 (see FIGS. 5A-5B) via a second connector attachment element 214a (see FIGS. 5A-5B).

As shown in FIG. 5B, the first end 205a of each first connector portion 204 is preferably attached to the axial actuator arm 210, and the second end 205b of each first connector portion 204 is preferably attached to a fixed platform portion 216a (see also FIG. 5C) positioned at the second end portion 74 of the structural frame assembly 70. As further shown in FIG. 5B, the body 206 of each first connector portion 204 is preferably positioned at a location 218 underneath the mounting assembly 154 of the third pivotal linkage assembly 150.

As shown in FIG. 5B, the first end 208a of each second connector portion 207 is preferably attached to the axial actuator arm 210, and the second end 208b of each second connector portion 207 is preferably attached to a vertical actuator arm 226, discussed in further detail below. As further shown in FIG. 5B, the body 209 of each second connector portion 207 is preferably positioned at a location 219 underneath the flexible aerodynamic member 12, such as the rotor blade 12a.

As shown in FIGS. 5A-5B, the fourth pivotal linkage assembly further comprises a pair of vertical actuator link assemblies 220 configured for actuation by the pair of vertical actuators 192, respectively. The pair of vertical actuator link assemblies 220 (see FIG. 5A) comprise a first vertical actuator link assembly 220a (see FIGS. 5A-5B) and a second vertical actuator link assembly 220b (see FIG. 5A) opposite the first vertical actuator link assembly 220a. As shown in FIGS. 5A-5B, the first and second vertical actuator link assemblies 220a, 220b preferably each comprises dual L-shaped link members 222a, 222b, a base connector portion 224, and a vertical actuator arm 226. As further shown in FIGS. 5A-5B, the dual L-shaped link members 222a, 222b each has a first end 228a coupled to the vertical actuator load cell 198 via a first link attachment 230a, a second end 228b coupled to the vertical actuator arm 226 via a second link attachment 230b, and an angled portion 232 pivotally attached to the base connector portion 224 via a pivot pin 234.

As further shown in FIG. 5B, each vertical actuator arm 226 is attached at a lower end 236a to the second end 228b of each of the dual L-shaped link members 222a, 222b, and is attached at an upper end 236b to the second connector portion 207 via a second connector attachment element 214b. Thus, as shown in FIG. 5B, the second connector portion 207 connects the vertical actuator arm 226 to the axial actuator arm 210.

As shown in FIG. 5A, the base connector portion 224 is preferably connected to a fixed platform portion 216b at the intermediate portion 76 of the structural frame assembly 70. As further shown in FIG. 5A, the vertical actuators 192 are preferably connected to the fixed platform portion 216c at the intermediate portion 76 of the structural frame assembly 70.

The pair of axial actuators 184 (see FIGS. 5A-5C) function as axial loading members 174 (see FIGS. 5C, 8) and are operably coupled, via the pair of axial actuator load cells 190 (see FIGS. 5A-5C) and via the axial actuator link assemblies 200 (see FIGS. 5A-5C), to the vertical actuator link assemblies 220 (see FIGS. 5A-5B), and in turn, to the flexible aerodynamic member 12 (see FIGS. 5A-5C), such as the rotor blade 12a (see FIGS. 5A-5C), to apply axial load 64a (see FIG. 8) to the one or more load distribution weighted elements 182 (see FIGS. 5A-5C) disposed within the flexible aerodynamic member 12, such as the rotor blade 12a.

In addition, as shown in FIGS. 5A-5B, the pair of vertical actuators 192 are operably coupled via the pair of vertical actuator load cells 198, to the vertical actuator link assemblies 220, and in turn, to the flexible aerodynamic member 12, such as the rotor blade 12a, to apply a vertical load 64c (see FIG. 8) to the one or more load distribution weighted elements 182 disposed within the flexible aerodynamic member 12, such as the rotor blade 12a. As shown in FIG. 5B, the vertical actuator arms 226 are preferably positioned at a location 238 directly underneath the one or more load distribution weighted elements 182 disposed within the flexible aerodynamic member 12, such as the rotor blade 12a.

In this embodiment, a plurality of axial loading members 174 (see FIGS. 7, 8), such as chord actuators 166 (see FIGS. 5C, 7, 8) and axial actuators 184 (see FIGS. 5C, 8), provide an axial load 64a (see FIG. 8) on the one or more load distribution weighted elements 182 (see FIGS. 5A-5C, 8), to enable a distributed load 64b (see FIG. 8) on the outboard end portion 28 (see FIGS. 5A-5C), or tip, of the flexible aerodynamic member 12 (see FIGS. 5A-5C, 8), such as the rotor blade 12a (see FIGS. 5A-5C, 8). In addition, in this embodiment, a plurality of torsional reaction members 176, such as the flap reaction links 288 (see FIGS. 7, 8), react a torsional reaction 178 (see FIG. 8) of the outboard end portion 28 (see FIGS. 5A-5C), or tip, of the flexible aerodynamic member 12 (see FIGS. 5A-5C, 8), such as the rotor blade 12a (see FIGS. 5A-5C, 8), when the plurality of axial loading members 174 (see FIGS. 7, 8) apply the axial load 64a (see FIG. 8) on the one or more load distribution weighted elements 182 (see FIGS. 5A-5C, 8). Further, moment balancing members 146 (see FIGS. 6A, 8), such as flap actuators 140 (see FIGS. 6A, 8), apply an axial load 64a (see FIG. 8) on the second pivot arm assembly 130 (see FIGS. 6A, 8), which, in turn, applies a balancing force 148 (see FIG. 8) to balance a moment 116 (see FIG. 8), such as the flap bending moment 116b (see FIG. 8), induced on the flexible aerodynamic member 12 (see FIGS. 5A-5C, 8), such as the rotor blade 12a (see FIGS. 5A-5C, 8), by the plurality of axial loading members 174 (see FIGS. 7, 8), such as the chord actuators 166 (see FIGS. 5C, 7, 8) and the axial actuators 184 (see FIGS. 5C, 8). In addition, the axial reaction member 108 (see FIGS. 4A-4D, 6A-6B, 8) is preferably configured to react the plurality of axial loading members 174 (see FIGS. 7, 8), such as the chord actuators 166 (see FIGS. 5C, 7, 8) and the axial actuators 184 (see FIGS. 5C, 8).

Figure 6A:
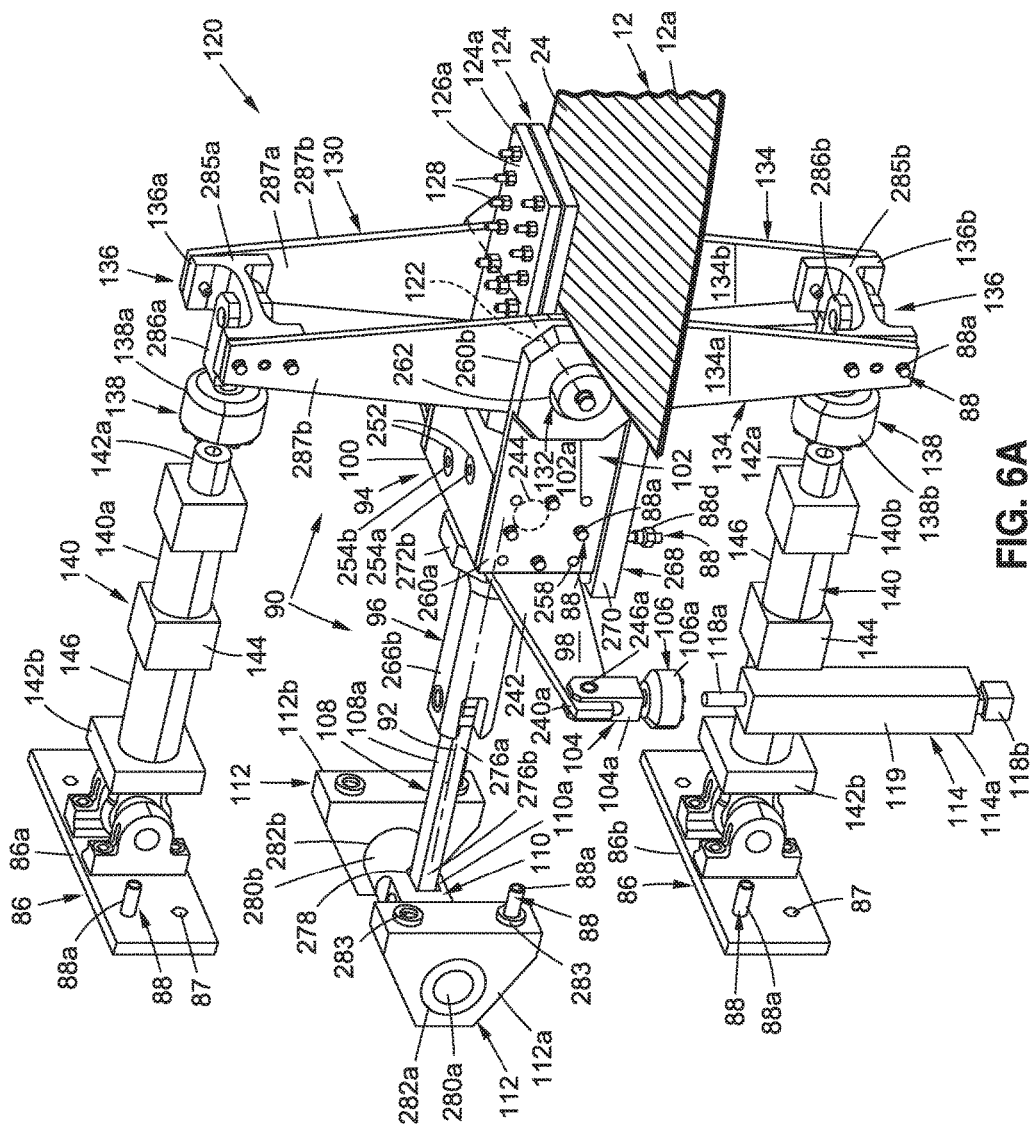
FIG. 6A is an illustration of an enlarged front perspective view of a first pivotal linkage assembly, of FIGS. 4A and 5A, operably coupled to a pitch actuator, and a second pivotal linkage assembly, of FIGS. 4A and 5A, operably coupled to the pair of flap actuators.
Figure 6B:
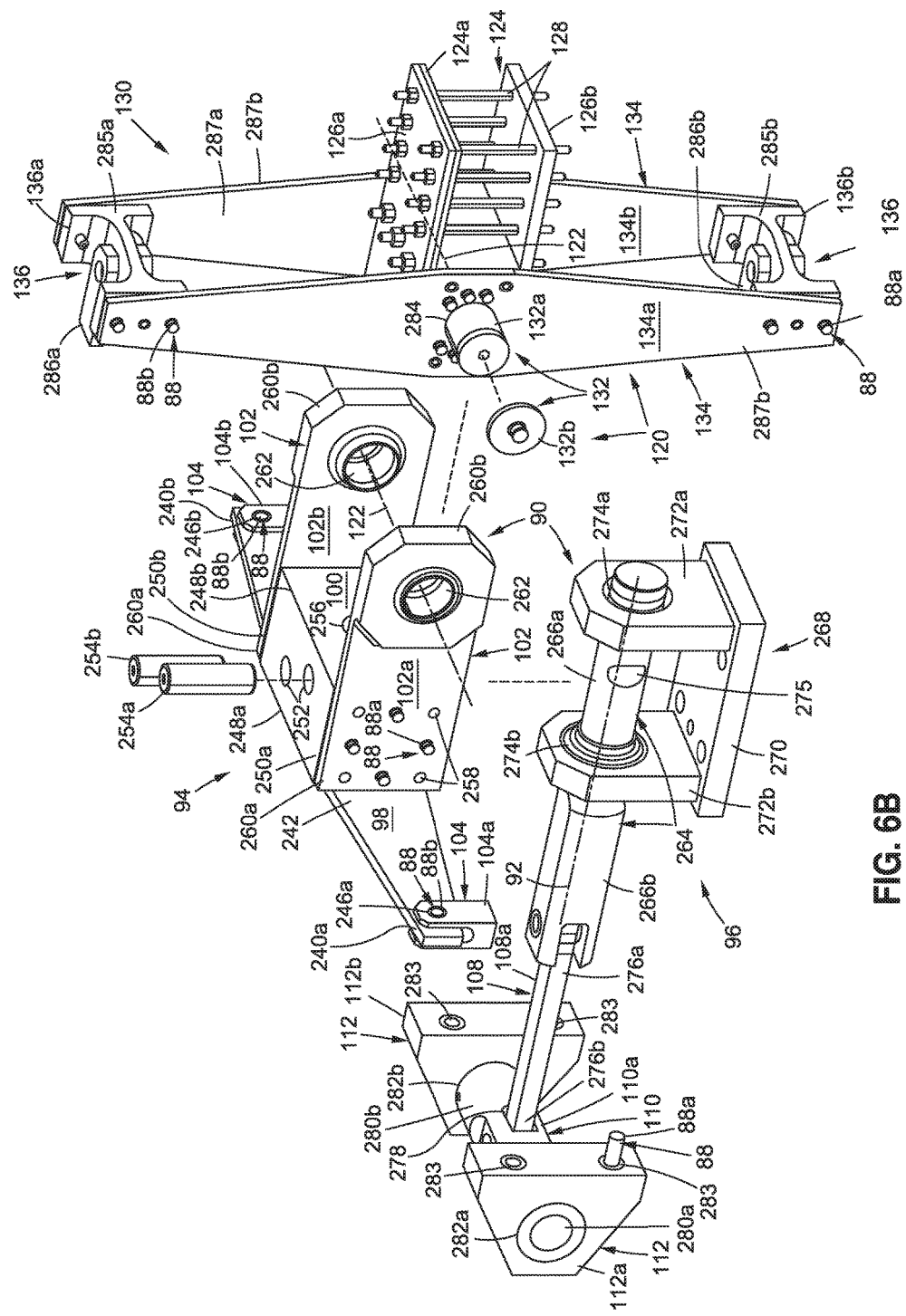
FIG. 6B is an illustration of an exploded front perspective view of the first pivotal linkage assembly and the second pivotal linkage assembly of FIG. 6A.

Now referring to FIGS. 6A-6B, FIG. 6A is an illustration of an enlarged front perspective view of the first pivotal linkage assembly 90, of FIGS. 4A and 5A, operably coupled to a pitch actuator 114, such as in the form of first pitch actuator 114a, and is an illustration of an enlarged front perspective view of the second pivotal linkage assembly 120, of FIGS. 4A and 5A, operably coupled to the pair of flap actuators 140, such as in the form of upper flap actuator 140a and lower flap actuator 140b. FIG. 6B is an illustration of an exploded front perspective view of the first pivotal linkage assembly 90 and the second pivotal linkage assembly 120 of FIG. 6A.

FIGS. 6A-6B show the first pivotal linkage assembly 90 comprising the first pivot arm assembly 94 pivotally coupled to the first pin joint 96 and pivotable about the pitch axis 92. FIGS. 6A-6B further show the horizontal arm 98, the first pin joint link 100 attached to the horizontal arm 98, and the pair of side plates 102 attached to the first pin joint link 100.

The horizontal arm 98 (see FIGS. 6A-6B) comprises a first end 240a (see FIGS. 6A-6B), a second end 240b (see FIG. 6B), and a body 242 (see FIGS. 6A-6B) formed between the first end 240a and the second end 240b. The horizontal arm 98 (see FIGS. 6A-6B) preferably has a central opening 244 (see FIG. 6A) configured to receive the first pin joint 96 (see FIG. 6A). The horizontal arm 98 (see FIGS. 6A-6B) preferably has a first end opening 246a (see FIGS. 6A-6B) and second end opening 246b (see FIG. 6B) opposite the first end opening 246a. Each of the first and second end openings 246a, 246b (see FIG. 6B) is configured to receive an attachment element 88 (see FIG. 6B), such as a pin 88b (see FIG. 6B), or another suitable attachment element 88.

As shown in FIG. 6B, a first pitch actuator lug 104a is coupled to the first end 240a of the horizontal arm 98 via the attachment element 88 inserted through the end opening 246a, and a second pitch actuator lug 104b is coupled to the second end 240b of the horizontal arm 98 via the attachment element 88 inserted through the end opening 246b. As shown in FIG. 6A, the first pitch actuator lug 104a is coupled to the first pitch actuator load cell 106a, and the first pitch actuator load cell 106a is operably coupled to the upper end 118a of the pitch actuator 114, such as the first pitch actuator 114a. FIG. 6A shows the pitch actuator 114, such as the first pitch actuator 114a, with the upper end 118a, the lower end 118b, and the body 119. A second pitch actuator 114b (see FIG. 5D) is positioned parallel to and opposite from the first pitch actuator 114a (see FIG. 5D).

As shown in FIG. 6B, the first pin joint link 100 has a first end 248a attached to the body 242 of the horizontal arm 98, and has a second end 248b that faces the second pivotal linkage assembly 120. As further shown in FIG. 6B, the first pin joint link 100 has a first side 250a attached to the first side plate 102a, and a second side 250b attached to the second side plate 102b, where the first side 250a is opposite the second side 250b. The first pin joint link 100 (see FIG. 6B) preferably has a central opening 256 (see FIG. 6B) configured to receive the first pin joint 96 (see FIG. 6B) after the first pin joint 96 is inserted through the central opening 244 (see FIG. 6A) of the horizontal arm 98 (see FIGS. 6A-6B).

As shown in FIGS. 6A-6B, the first pin joint link 100 may have through openings 252 formed through the top of the first pin joint link 100. The through openings 252 (see FIGS. 6A-6B) are preferably configured to receive a first link pin 254a and a second link pin 252b, respectively. The first and second link pins 254a, 254b (see FIGS. 6A-6B) are preferably cylindrical in shape and designed to couple with the first pin joint 96 (see FIGS. 6A-6B).

As shown in FIGS. 6A-6B, the first and second side plates 102a, 102b are attached to the first and second sides 250a, 205b of the first pin joint link 100 (see FIGS. 6A-6B), via a plurality of attachment elements 88 (see FIGS. 6A-6B), such as bolts 88a (see FIGS. 6A-6B), configured for insertion through a plurality of side plate holes 258 (see FIGS. 6A-6B). As shown in FIG. 6B, each of the first and second side plates 102a, 120b has a first end 260a coupled or attached to the horizontal arm 98 and to the respective first and second sides 250a, 250b of the first pin joint link 100, and each of the first and second side plates 102a, 120b has a second end 260b with a through opening 262 configured for insertion of a pin portion 132a of the second pin joint 132 of the second pivotal linkage assembly 120.

FIG. 6A shows the first pin joint 96 coupled to and assembled with the first pivot arm assembly 94. FIG. 6B shows the first pin joint 96 uncoupled and unassembled from the first pivot arm assembly 94. As shown in FIG. 6B, the first pin joint 96 comprises a pitch shaft 264 having a first guide end portion 266a and a second reaction end portion 266b, and further comprising a retaining apparatus 268 for retaining the first guide end portion 266a of the pitch shaft 264. As further shown in FIG. 6B, the retaining apparatus 268 comprises a base plate 270 with first and second end walls 272a, 272b attached to the base plate 270. The first and second end walls 272a, 272b extend upwardly from the base plate 270 and are spaced parallel to and opposite each other. The first end wall 272a (see FIG. 6B) has a first through opening 274a (see FIG. 6B), and the second end wall 272b (see FIG. 6B) has a second through openings 274b (see FIG. 6B). The first and second through openings 274a, 274b (see FIG. 6B) are configured to receive the first guide end portion 266a (see FIG. 6B) of the pitch shaft 264 (see FIG. 6B). As shown in FIG. 6B, the first guide end portion 266a of the pitch shaft 264 may have a recessed portion 275 formed on each side of the first guide end portion 266a, each recessed portion 275 configured to receive and abut the first and second link pins 254a, 254b, respectively.

As further shown in FIGS. 6A-6B, the second reaction end portion 266b of the pitch shaft 264 is coupled to the axial reaction member 108, such as in the form of a tie bar 108a. The axial reaction member 108 (see FIGS. 6A-6B) has a first end 276a (see FIGS. 6A-6B) coupled to the second reaction end portion 266b (see FIGS. 6A-6B) of the pitch shaft 264 (see FIGS. 6A-6B), and has a second end 276b (see FIGS. 6A-6B) coupled to the pin 110 (see FIGS. 6A-6B), such as the trunnion pin 110a (see FIGS. 6A-6B). As shown in FIGS. 6A-6B, the second end 276b is preferably inserted into and retained in a slot opening 278 of the pin 110, such as the trunnion pin 110a.

As further shown in FIGS. 6A-6B, the pin 110, such as the trunnion pin 110a, has a first end 280a inserted into a first coupling opening 282a of the first coupling 112a, and has a second end 280b inserted into a second coupling opening 282b of the second coupling 112b. The first and second couplings 112a, 112b (see FIGS. 6A-6B) may each further have one or more attachment openings 283 (see FIGS. 5D, 6A-6B) configured to receive one or more attachment elements 88 (see FIGS. 5D, 6A-6B), such as in the form of bolts 88a (see FIGS. 5D, 6A-6B), or another suitable attachment element, for attaching the first and second couplings 112a, 112b (see FIGS. 5D, 6A-6B) to the first end portion 72 (see FIG. 5D) of the structural frame assembly 70 (see FIG. 5D).

Figure 7:
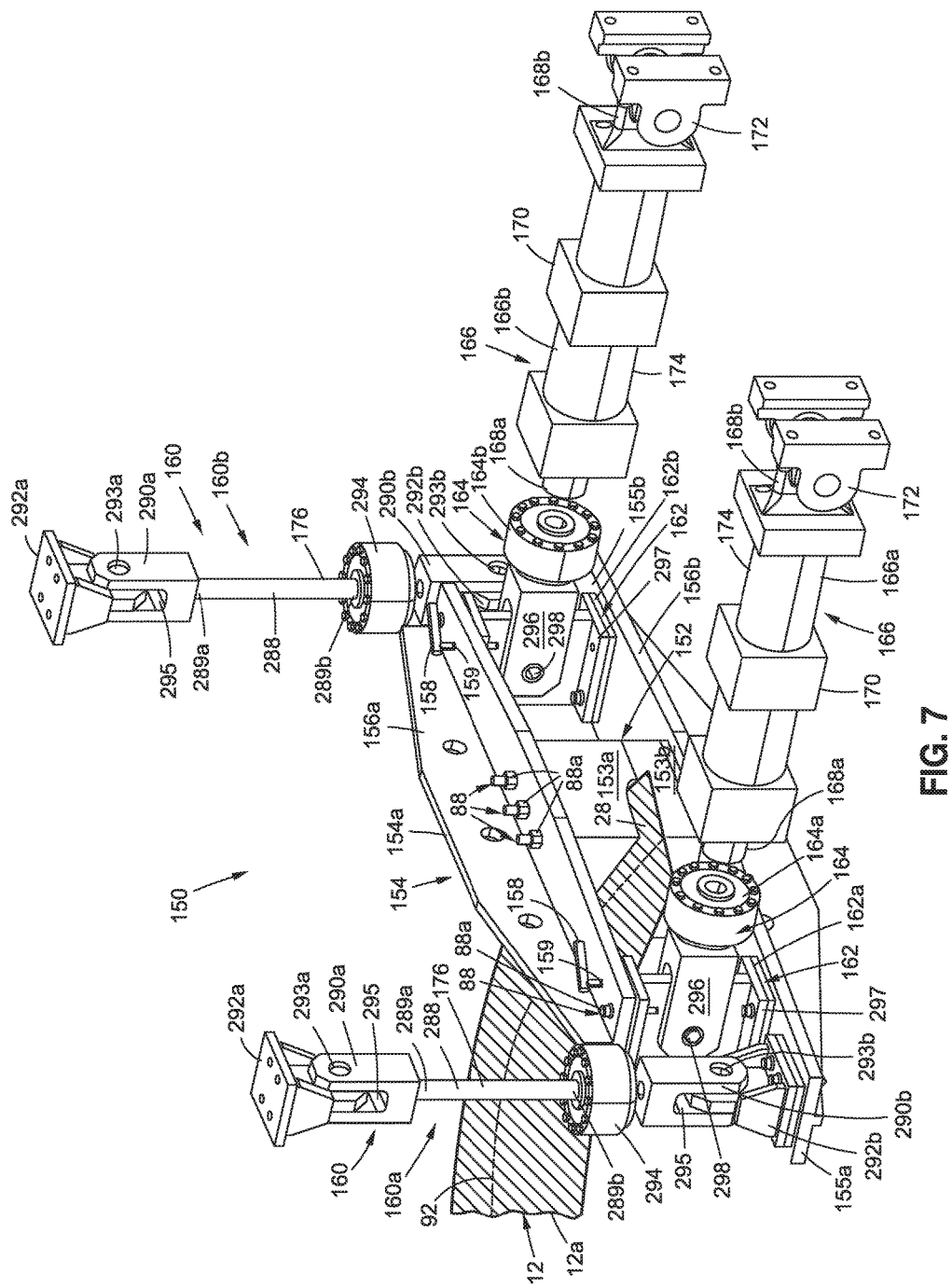
FIG. 7 is an illustration of an enlarged front perspective view of a third pivotal linkage assembly, of FIGS. 4B and 5A, operably coupled to a pair of chord actuators.

The axial reaction member 108 (see FIGS. 6A-6B), such as the tie bar 108a (see FIGS. 6A-6B), is designed to hold back the flexible aerodynamic member 12 (see FIGS. 4B, 5A), such as the rotor blade 12a (see FIGS. 4B, 5A), when axial load 62a (see FIG. 8), or centrifugal load, is applied at the third pivotal linkage assembly 150 (see FIGS. 4B, 5A, 7). The axial reaction member 108 (see FIGS. 6A-6B) may also comprise another suitable bar or elongated structure.

As further shown in FIGS. 6A-6B, the second pivotal linkage assembly 120 comprises the second pivot arm assembly 130 pivotally coupled to the second pin joint 132 and pivotable about the flap axis 122. The second pivot arm assembly 130 (see FIGS. 6A-6B) comprises the pair of vertical arms 134 (see FIGS. 6A-6B), such as in the form of the first vertical arm 134a (see FIGS. 6A-6B) and the second vertical arm 134b (see FIGS. 6A-6B), each attached via the second pin joint 132 (see FIGS. 6A-6B) to the first pivotal linkage assembly 90 (see FIGS. 6A-6B). The first vertical arm 134a (see FIGS. 6A-6B) and the second vertical arm 134b (see FIGS. 6A-6B) each has an inner side 287a (see FIGS. 6A-6B) and an outer side 287b (see FIGS. 6A-6B). As shown in FIG. 6B, the second pin joint 132 comprises a pin portion 132a and a pin end cap portion 132b attached to the pin portion 132a, and is configured for insertion through a central opening 284 in each of the first and second vertical arms 134a, 134b.

As shown in FIGS. 6A-6B, the second pivot arm assembly 130 further comprises the pair of flap link assemblies 136, such as the upper flap link assembly 136a and the lower flap link assembly 136b, attached to the pair of vertical arms 134, such as the first vertical arm 134a and the second vertical arm 134b, respectively. The upper flap link assembly 136a (see FIGS. 6A-6B) comprises an upper flap link 285a (see FIGS. 6A-6B) coupled to an upper flap lug 286a (see FIGS. 6A-6B), and the lower flap link assembly 136b (see FIGS. 6A-6B) comprises a lower flap link 285b (see FIGS. 6A-6B) coupled to a lower flap lug 286b (see FIGS. 6A-6B). The upper flap link 285a (see FIGS. 6A-6B) and the lower flap link 285b (see FIGS. 6A-6B) are attached to and between the inner sides 287a (see FIGS. 6A-6B) of the first and second vertical arms 134a, 134b (see FIGS. 6A-6B), via a plurality of attachment elements 88 (see FIGS. 6A-6B), such as in the form of bolts 88a (see FIGS. 6A-6B), or other suitable attachment elements. When assembled, the second ends 260b (see FIGS. 6A-6B) of the first and second side plates 102a, 102b (see FIGS. 6A-6B) of the first pivotal linkage assembly 90 (see FIGS. 6A-6B) are coupled to the outer sides 287b (see FIGS. 6A-6B) around the central opening 284 (see FIG. 6B) of the vertical arms 134 (see FIGS. 6A-6B) of the second pivotal linkage assembly 120 (see FIGS. 6A-6B), and the second pin joint 132 (see FIGS. 6A-6B) couples the side plates 102 (see FIGS. 6A-6B) to the vertical arms 134 (see FIGS. 6A-6B).

As further shown in FIG. 6A, the first holding apparatus 124, such as in the form of clamp plate apparatus 124a, is coupled between the inner sides 287a of the vertical arms 134, preferably above and below the second pin joint 132, in order to hold or clamp in place the inboard end portion 24 (see FIG. 6A) of the flexible aerodynamic member 12 (see FIG. 6A), such as the rotor blade 12a (see FIG. 6A). The first holding apparatus 124 (see FIGS. 6A-6B), such as in the form of clamp plate apparatus 124a (see FIGS. 6A-6B) preferably comprises one or more upper clamp plates 126a (see FIGS. 5B, 6A-6B) and one or more lower clamp plates 126b (see FIGS. 4A, 5B) attached together with a plurality of clamp plate attachments 128 (see FIGS. 5B, 6A-6B).

As shown in FIG. 6A, the flap actuator load cell 138, such as the upper flap actuator load cell 138a, is coupled to the upper flap lug 286a, and the flap actuator load cell 138, such as the lower flap actuator load cell 138b, is coupled to the lower flap lug 286b.

FIG. 6A shows the flap actuators 140, such as the upper flap actuator 140a and the lower flap actuator 140b. Each of the upper and lower flap actuators 140a, 140b (see FIG. 6A) comprises the first end 142a (see FIG. 6A), the second end 142b (see FIG. 6A), and the body 144 (see FIG. 6A) formed between the first end 142a (see FIG. 6A) and the second end 142b (see FIG. 6A). The first end 142 (see FIG. 6A) of the flap actuator 140 (see FIG. 6A), such as the upper flap actuator 140a (see FIG. 6A), is operably coupled to the upper flap actuator load cell 138a (see FIG. 6A), and the first end 142a of the flap actuator 140 (see FIG. 6A), such as the lower flap actuator 140b (see FIG. 6A), is operably coupled to the lower flap actuator load cell 138b (see FIG. 6A). As shown in FIG. 6A, the second end 142b of the upper flap actuator 140a is attached to the actuator reaction plate 86, such as the upper flap actuator reaction plate 86a, and the second end 142b of the lower flap actuator 140b is attached to the actuator reaction plate 86, such as the lower flap actuator reaction plate 86b. The upper and lower flap actuator reaction plates 86a, 86b (see FIG. 6A) have actuator reaction plate holes 87 (see FIG. 6A) configured to receive attachment elements 88 (see FIG. 6A), such as bolts 88a (see FIG. 6A), or another suitable attachment element, for attaching the upper and lower flap actuator reaction plates 86a, 86b (see FIGS. 5D, 6A) to the first end portion 72 (see FIG. 5D) of the structural frame assembly 70 (see FIG. 5D).

As discussed above, the pair of flap actuators 140 (see FIG. 6A) function as moment balancing members 146 (see FIG. 6A) and are configured to apply a moment 116 (see FIG. 8), such as in the form of a flap bending moment 116b (see FIG. 8), to the second pivot arm assembly 130 (see FIG. 6A) of the second pivotal linkage assembly 120 (see FIG. 6A).

Now referring to FIG. 7, FIG. 7 is an illustration of an enlarged front perspective view of the third pivotal linkage assembly 150 of FIGS. 4B and 5A, operably coupled to the pair of chord actuators 166, such as in the form of first chord actuator 166a and second chord actuator 166b. FIG. 7 shows the third pivotal linkage assembly 150 with the second holding apparatus 152 holding or securing the outboard end portion 28, or tip, of the flexible aerodynamic member 12, such as the rotor blade 12a. The third pivotal linkage assembly 150 (see FIG. 7) is pivotable about the pitch axis 92 (see FIG. 7).

As shown in FIG. 7, the second holding apparatus 152 preferably comprises one or more upper clamp plates 153a attached to one or more lower clamp plates 153b. As further shown in FIG. 7, the upper clamp plate 153a and the lower clamp plate 153b are configured to clamp down on the outboard end portion 28, or tip, of the flexible aerodynamic member 12, such as the rotor blade 12a. Alternatively, the second holding apparatus 152 (see FIG. 7) may comprise another suitable holding apparatus or device.

The third pivotal linkage assembly 150 (see FIG. 7) comprises the mounting assembly 154 (see FIG. 7), such as in the form of weldment assembly 154a (see FIG. 7), or another suitable mounting assembly, having the removable upper piece 156a (see FIG. 7) and the fixed lower piece 156b (see FIG. 7). The mounting assembly 154 (see FIG. 7) has a first end 155a (see FIG. 7) and a second end 155b (see FIG. 7). The mounting assembly 154 (see FIG. 7) further comprises alignment pins 158 (see FIGS. 4B, 5A, 5D, 7) configured for insertion through alignment pin holes 159 (see FIG. 7) formed in the removable upper piece 156a (see FIG. 7). The alignment pins 158 (see FIG. 7) are preferably L-shaped, or another suitable shape, and may be used to facilitate alignment of the removable upper piece 156a (see FIG. 7) with the fixed lower piece 156b (see FIG. 7), when the removable upper piece 156a is attached in place. A plurality of attachment elements 88 (see FIGS. 4B, 5A, 7), such as in the form of bolts 88a (see FIGS. 4B, 5A, 7), or another suitable attachment element 88, may be used to attach the removable upper piece 156a (see FIG. 7) to the upper clamp plate 153a (see FIG. 7) of the second holding apparatus 152 (see FIG. 7). As shown in FIG. 7, the second holding apparatus 152 is positioned and attached between the removable upper piece 156a and the fixed lower piece 156b of the mounting assembly 154.

As shown in FIG. 7, the third pivotal linkage assembly 150 further comprises the pair of flap reaction link assemblies 160 attached to the mounting assembly 154. The pair of flap reaction link assemblies 160 (see FIG. 7) preferably comprises the first flap reaction link assembly 160a (see FIG. 7) and the second flap reaction link assembly 160b (see FIG. 7) positioned opposite the first flap reaction link assembly 160a. As further shown in FIG. 7, the first flap reaction link assembly 160a is attached at the first end 155a of the mounting assembly 154, and the second flap reaction link assembly 160b is attached at the second end 155b of the mounting assembly 154, opposite the first flap reaction link assembly 160a. Each of the first and second flap reaction link assemblies 160a, 160b (see FIG. 7) comprises a flap reaction link 288 having an upper end 289a (see FIG. 7) and a lower end 289b (see FIG. 7).

As shown in FIG. 7, the upper end 289a of each of the first and second flap reaction link assemblies 160a, 160b is connected to an upper flap reaction link lug 290a, which is coupled to an upper flap reaction link lug connector 292a, via an upper flap reaction link pivot pin 293a. The upper flap reaction link lug connector 292a (see FIG. 7) is configured for insertion into a U-shaped slot 295 (see FIG. 7) of the upper flap reaction link lug 290a (see FIG. 7). Each of the upper flap reaction link lug connectors 292a (see FIGS. 5A, 7) is configured for attachment to a cross support structure 82 (see FIGS. 4A, 5B) attached at or near the second end portion 74 (see FIGS. 4B, 5A) of the structural frame assembly 70 (see FIGS. 4B, 5A).

As further shown in FIG. 7, the lower end 289b of each of the first and second flap reaction link assemblies 160a, 160b is connected to a flap reaction link load cell 294. The flap reaction link load cell 294 (see FIG. 7) of each of the first and second flap reaction link assemblies 160a, 160b (see FIG. 7) is connected to a lower flap reaction link lug 290b (see FIG. 7), which is coupled to a lower flap reaction link lug connector 292b (see FIG. 7), via a lower flap reaction link pivot pin 293b (see FIG. 7). The lower flap reaction link lug connector 292b (see FIG. 7) is configured for insertion into a U-shaped slot 295 (see FIG. 7) of the lower flap reaction link lug 290b (see FIG. 7). Each of the lower flap reaction link lug connectors 292b (see FIGS. 4B, 5A, 7) is connected to the first and second ends 155a, 155b (see FIG. 7), respectively, of the mounting assembly 154 (see FIG. 7).

The third pivotal linkage assembly 150 (see FIG. 7) may further comprise a pair of chord actuator lug assemblies 162 (see FIG. 7) attached to the mounting assembly 154 (see FIG. 7). The pair of chord actuator lug assemblies 162 (see FIG. 7) preferably comprises the first chord actuator lug assembly 162a (see FIG. 7), and the second chord actuator lug assembly 162b (see FIG. 7) positioned opposite the first chord actuator lug assembly 162a. As shown in FIG. 7, the first chord actuator lug assembly 162a is positioned on one side of the second holding apparatus 152, and the second chord actuator lug assembly 162b is positioned on the other side of the second holding apparatus 152. The first chord actuator lug assembly 162a (see FIG. 7) and the second chord actuator lug assembly 162b (see FIG. 7) are preferably positioned and attached between the removable upper piece 156a and the fixed lower piece 156b of the mounting assembly 154.

Each of the first and second chord actuator lug assemblies 162a, 162b (see FIG. 7), comprises a chord actuator lug 296 (see FIG. 7) attached to a chord actuator lug connector 297 (see FIG. 7), via a chord actuator pivot pin 298 (see FIG. 7). As shown in FIG. 7, the bottom of each chord actuator lug connector 297 is attached to the top of the fixed lower piece 156b of the mounting assembly 154, and the top of each chord actuator lug connector 297 is attached to the bottom of the removable upper piece 156a of the mounting assembly 154.

The third pivotal linkage assembly 150 (see FIG. 7) further comprises a pair of chord actuator load cells 164 (see FIG. 7) coupled to the pair of chord actuator lug assemblies 162 (see FIG. 7), respectively. The pair of chord actuator load cells 164 (see FIG. 7) preferably comprises the first chord actuator load cell 164a (see FIG. 7), and the second chord actuator load cell 164b (see FIG. 7) positioned opposite the first chord actuator load cell 162a. As shown in FIG. 7, the chord actuator lug 296 of the first chord actuator lug assembly 162a is attached to one end of the first chord actuator load cell 164a, and the chord actuator lug 296 of the second chord actuator lug assembly 162b is attached to one end of the second chord actuator load cell 164b.

As shown in FIG. 7, the pair of chord actuators 166 comprises the first chord actuator 166a and the second chord actuator 166b, and the pair of chord actuators 166 are operably coupled to the third pivotal linkage assembly 150 to apply an axial load 64a (see FIG. 8) to the flexible aerodynamic member 12, via the third pivotal linkage assembly 150. FIG. 7 shows the first chord actuator 166a and the second chord actuator 166b each having the first end 168a, the second end 168b, and the body 170 formed between the first end 168a and the second end 168b. As shown in FIG. 7, the first end 168a of the first chord actuator 166a is configured to couple to, and during testing 63 (see FIG. 8), is operably coupled to, the first chord actuator load cell 164a, and the first end 168a of the second chord actuator 166b is configured to couple to, and during testing 63 (see FIG. 8), is operably coupled to, the second chord actuator load cell 164b. As further shown in FIG. 7, the second end 168b of each of the first and second chord actuators 166a, 116b is attached to a bracket attachment 172. The bracket attachments 172 are configured for attachment to the actuator reaction plate 86 (see FIGS. 4B, 5A), such as the chord actuator reaction plate 86c (see FIGS. 4B, 5A), at the second end portion 74 (see FIGS. 4B, 5A) of the structural frame assembly 70 (see FIGS. 4B, 5A).

As discussed above, the pair of chord actuators 166 (see FIG. 7) function as axial loading members 174 (see FIG. 7) configured to apply axial load 64a (see FIGS. 4B, 8) to the flexible aerodynamic member 12 (see FIGS. 4B, 5A), via the third pivotal linkage assembly 150. In addition, the pair of flap reaction link assemblies 160 (see FIG. 7), and in particular, the flap reaction links 288 (see FIG. 7), function as torsional reaction members 176 (see FIG. 7) configured to react a torsional reaction 178 (see FIG. 8) of the outboard end portion 28 (see FIG. 7), or tip, of the flexible aerodynamic member 12 (see FIG. 7), when the pair of chord actuators 166 (see FIG. 7) apply the axial load 64a (see FIGS. 4B, 8) to the flexible aerodynamic member 12 (see FIG. 7).

Figure 8:
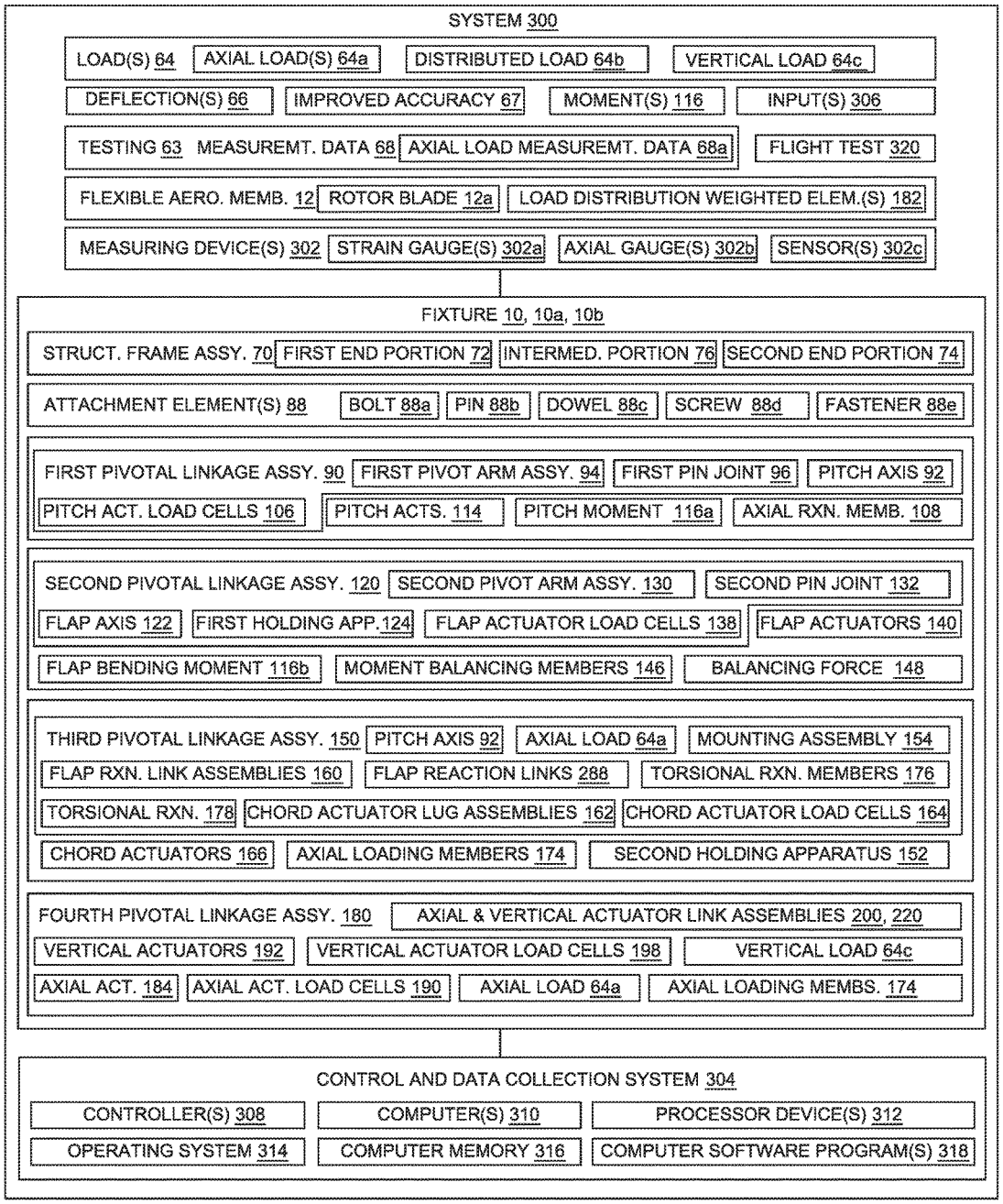
FIG. 8 is an illustration of a functional block diagram of an exemplary embodiment of a system of the disclosure.

During testing, the flap bending moment 116b (see FIG. 8) is created by the flap actuators 140 (see FIGS. 4B, 5A) and input into the inboard end portion 24 (see FIGS. 1, 4B, 5A) of the flexible aerodynamic member 12, such as the rotor blade 12a, and the flap bending moment 116b (see FIG. 8) gets reacted down to zero at the outboard end portion 28, or tip, of the flexible aerodynamic member 12, such as the rotor blade 12a, and comes out as a reaction through the flap reaction links 288 (see FIGS. 7, 8) of the third pivotal linkage assembly 150 (see FIGS. 7, 8). The pitch moment 116a (see FIG. 8), or rotation or torque, is created by the pitch actuators 114 (see FIGS. 4B, 5A) and input into the inboard end portion 24 (see FIGS. 1, 4B, 5A) of the flexible aerodynamic member 12, such as the rotor blade 12a, and the pitch moment 116a (see FIG. 8) gets coupled out through the flap reaction links 288 (see FIGS. 7, 8) of the third pivotal linkage assembly 150 (see FIGS. 7, 8).

Now referring to FIG. 8, in another embodiment, there is provided a system 300 for testing 63 (see FIG. 8) one or more loads 64 (see FIG. 8), such as one or more axial loads 64a (see FIG. 8), in a flexible aerodynamic member 12, such as a rotor blade 12a. FIG. 8 is an illustration of a functional block diagram of an exemplary embodiment of the system 300 of the disclosure. Embodiments of the system 300 are also shown in FIGS. 4B and 5A-5D.

As shown in FIG. 8, the system 300 comprises a fixture 10. The fixture 10 (see FIG. 8) may be in the form of fixture 10a (see FIGS. 4A-4B, 8), in the form of fixture 10b (see FIGS. 5A-5D, 8), or in another suitable form. As discussed above, the fixture 10 (see FIGS. 4B, 5A, 8) comprises the structural frame assembly 70 (see FIGS. 4B, 5A, 8) having the first end portion 72 (see FIGS. 4B, 5A, 8), the second end portion 74 (see FIGS. 4B, 5A, 8), and the intermediate portion 76 (see FIGS. 4B, 5A, 8) formed between the first end portion 72 and the second end portion 74. The parts of the structural frame assembly 70 (see FIGS. 4B, 5A, 8) are discussed in detail above. The fixture 10 (see FIG. 8) may comprise one or more attachment elements 88 (see FIGS. 4B, 5A, 8), such as in the form of one or more bolts 88a (see FIGS. 4B, 5A, 8), a pins 88b (see FIGS. 6B, 8), dowels 88c (see FIG. 8), screws 88d (see FIGS. 6A, 8), fasteners 88e (see FIG. 8), or other suitable attachment elements, for attaching together various parts of the fixture 10.

As shown in FIG. 8, the fixture 10 of the system 300 comprises the first pivotal linkage assembly 90 (see also FIGS. 4B, 5A) attached to the first end portion 72 (see also FIGS. 4B, 5A), where the first pivotal linkage assembly 90 is pivotable about a pitch axis 92 (see also FIGS. 4A-4B, 5A, 6A). The first pivotal linkage assembly 90 (see FIG. 8) comprises the first pivot arm assembly 94 (see FIG. 8) pivotally coupled to the first pin joint 96 (see FIG. 8). The first pin joint 96 (see FIG. 8) is coupled to the axial reaction member 108 (see FIG. 8). As discussed in detail above, the first pivot arm assembly 94 (see FIGS. 4B, 5D, 6A, 8) comprises the horizontal arm 98 (see FIGS. 4B, 5D, 6A) coupled to the pair of pitch actuator lugs 104 (see FIGS. 4B, 5D, 6A) and the pair of pitch actuator load cells 106 (see FIGS. 4B, 5D, 6A, 8). The first pivot arm assembly 94 (see FIGS. 4B, 5D, 6A, 8) further comprises the first pin joint link 100 (see FIGS. 4B, 5A, 6A) attached to the horizontal arm 98 and the pair of side plates 102 (see FIGS. 4B, 5A, 6A) attached to the first pin joint link 100. The pair of pitch actuators 114 (see FIGS. 4B, 5A, 6A, 8) is operably coupled to the first pivotal linkage assembly 90 (see FIGS. 4B, 5A, 6A, 8), to apply the pitch moment 116a (see FIGS. 4A, 8) to the first pivotal linkage assembly 90.

As further shown in FIG. 8, the fixture 10 of the system 300 comprises the second pivotal linkage assembly 120 attached to the first pivotal linkage assembly 90, where the second pivotal linkage assembly 120 is pivotable about a flap axis 122 (see also FIGS. 4B, 5A, 6A), and the flap axis 122 (see also FIG. 6A) is perpendicular to the pitch axis 92 (see also FIG. 6A). The first holding apparatus 124 (see FIGS. 4B, 5A, 6A, 8) is coupled to the second pivot arm assembly 130 (see FIGS. 4B, 5A, 6A, 8).

The second pivotal linkage assembly 120 (see FIG. 8) comprises the second pivot arm assembly 130 (see FIG. 8) pivotally coupled to the second pin joint 132 (see FIG. 8). As discussed in detail above, the second pivot arm assembly 130 (see FIGS. 6A-6B, 8) comprises the pair of vertical arms 134 (see FIGS. 6A-6B) each attached via the second pin joint 132 (see FIGS. 6A-6B) to the first pivotal linkage assembly 90 (see FIGS. 6A-6B, 8). The second pivot arm assembly 130 (see FIGS. 6A-6B, 8) further comprises the pair of flap link assemblies 136 (see FIGS. 6A-6B) attached to the pair of vertical arms 134 (see FIGS. 6A-6B). The second pivot arm assembly 130 (see FIG. 6A, 8) further comprises the pair of flap actuator load cells 138 (see FIGS. 6A, 8) coupled to the pair of flap link assemblies 136 (see FIGS. 6A, 8). The pair of flap actuators 140 (see FIGS. 4B, 5A, 6A, 8) is operably coupled to the flap actuator load cells 138 (see FIGS. 4B, 5A, 6A, 8) of the second pivotal linkage assembly 120 (see FIGS. 4B, 5A, 6A, 8), to apply the flap bending moment 116b (see FIG. 8) to the second pivotal linkage assembly 120.

The pair of flap actuators 140 (see FIGS. 4B, 5A, 6A, 8) function as moment balancing members 146 (see FIGS. 6A, 8) and are configured to apply a moment 116 (see FIG. 8), such as the flap bending moment 116b (see FIGS. 4A, 8), to the second pivot arm assembly 130 (see FIGS. 4B, 5A, 6A, 8) of the second pivotal linkage assembly 120 (see FIGS. 4B, 5A, 6A). In addition, the second pivot arm assembly 130 (see FIGS. 4B, 5A, 6A, 8) applies a balancing force 148 (see FIG. 8) to balance the moment 116 (see FIG. 8) induced on the flexible aerodynamic member 12 (see FIGS. 4B, 5A, 8), such as the rotor blade 12a (see FIGS. 4B, 5A, 8), by the third pivotal linkage assembly 150 (see FIGS. 4A, 5B, 7, 8).

As further shown in FIG. 8, the fixture 10 of the system 300 comprises the third pivotal linkage assembly 150 (see also FIGS. 4A, 5B, 7) attached to the second end portion 74 (see also FIGS. 4A, 5B), where the third pivotal linkage assembly 150 is pivotable about the pitch axis 92 (see also FIGS. 4A, 5B, 7). As shown in FIG. 8, the third pivotal linkage assembly 150 comprises the mounting assembly 154, comprises the pair of flap reaction link assemblies 160, including flap reaction links 288, attached to the mounting assembly 154, comprises the pair of chord actuator lug assemblies 162 attached to the mounting assembly 154, and comprises the pair of chord actuator load cells 164 coupled to the pair of chord actuator lug assemblies 162. The second holding apparatus 152 (see FIGS. 4B, 5A, 7, 8) is coupled to the mounting assembly 154 (see FIGS. 4B, 5A, 7, 8) of the third pivot arm assembly 150 (see FIGS. 4B, 5A, 7, 8).

The pair of chord actuators 166 (see FIGS. 4A, 5B, 7, 8) is operably coupled to the pair of chord actuator load cells 164 (see FIGS. 4A, 5B, 7, 8), of the third pivotal linkage assembly 150 (see FIGS. 4A, 5B, 7, 8), to apply an axial load 64a (see FIGS. 4B, 8) to the flexible aerodynamic member 12 (see FIGS. 4B, 5A, 7, 8) via the third pivotal linkage assembly 150. As discussed above, the pair of chord actuators 166 (see FIGS. 7, 8) function as axial loading members 174 (see FIGS. 7, 8) configured to apply axial load 64a (see FIGS. 4B, 8) to the flexible aerodynamic member 12 (see FIGS. 4B, 5A, 7, 8), via the third pivotal linkage assembly 150, to enable a distributed load 64b (see FIG. 8) on the outboard end portion 28 (see FIGS. 4B, 5A), or tip, of the flexible aerodynamic member 12, such as the rotor blade 12a. In addition, the pair of flap reaction link assemblies 160 (see FIGS. 7, 8), and in particular, the flap reaction links 288 (see FIGS. 7, 8), function as torsional reaction members 176 (see FIG. 7) configured to react a torsional reaction 178 (see FIG. 8) of the outboard end portion 28 (see FIG. 7), or tip, of the flexible aerodynamic member 12 (see FIGS. 7, 8), when the pair of chord actuators 166 (see FIGS. 7, 8) apply the axial load 64a (see FIGS. 4B, 8) to the flexible aerodynamic member 12 (see FIGS. 7, 8).

As further shown in FIG. 8, the fixture 10 of the system 300 may further optionally comprise the fourth pivotal linkage assembly 180 (see also FIGS. 5A-5D) attached to the intermediate portion 76 (see also FIGS. 5A-5D) of the structural frame assembly 70 (see also FIGS. 5A-5D). As discussed in detail above, the fourth pivotal linkage assembly 180 (see FIGS. 5A-5D, 8) is preferably positioned underneath the flexible aerodynamic member 12 (see FIGS. 5A-5D, 8), such as the rotor blade 12a (see FIGS. 5A-5D, 8), when the flexible aerodynamic member 12, such as the rotor blade 12a, is mounted to, and positioned between, the first holding apparatus 124 (see FIGS. 5A-5D, 8) and the second holding apparatus 152 (see FIGS. 5A-5D, 8), and when the flexible aerodynamic member 12, such as the rotor blade 12a, has one or more load distribution weighted elements 182 (see FIGS. 5A-5D, 8) disposed within the flexible aerodynamic member 12, such as the rotor blade 12a.

The fourth pivotal linkage assembly 180 (see FIG. 8) comprises a pair of vertical actuators 192 (see FIG. 8) operably coupled via a pair of vertical actuator load cells 198 (see FIG. 8) and via a pair of vertical actuator link assemblies 220 (see FIG. 8), to apply vertical load 64c (see FIG. 8) to the one or more load distribution weighted elements 182 (see FIG. 8) of the flexible aerodynamic member 12 (see FIG. 8), such as the rotor blade 12a (see FIG. 8). The fourth pivotal linkage assembly 180 (see FIG. 8) further comprises a pair of axial actuators 184 (see FIG. 8) that function as axial loading members 174 (see FIG. 8), and that are operably coupled via a pair of axial actuator load cells 190 (see FIG. 8), via a pair of axial actuator link assemblies 200 (see FIG. 8), and via the pair of vertical actuator link assemblies 220 (see FIG. 8), to apply axial load 64a (see FIG. 8) to the one or more load distribution weighted elements 182 (see FIG. 8) of the flexible aerodynamic member 12 (see FIG. 8), such as the rotor blade 12a (see FIG. 8).

As further shown in FIG. 8, the system 300 further comprises the flexible aerodynamic member 12, such as in the form of rotor blade 12a, or another suitable blade or flexible aerodynamic member. Preferably, the flexible aerodynamic member 12 (see FIGS. 1, 4A, 5B, 8), such as in the form of rotor blade 12a (see FIGS. 1, 4A, 5B, 8), is for use in an air vehicle 14 (see FIG. 1), such as a rotorcraft 14a (see FIG. 1). The flexible aerodynamic member 12 (see FIGS. 4A, 5B, 8), such as in the form of rotor blade 12a (see FIGS. 4A, 5B, 8), is preferably installed in the fixture 10 (see FIGS. 4A, 5B, 8) with the inboard end portion 24 (see FIGS. 4A, 5B) mounted to the first holding apparatus 124 (see FIGS. 4A, 5B, 8) of the second pivotal linkage assembly 120 (see FIGS. 4A, 5B, 8), and with the outboard end portion 28 (see FIGS. 4A, 5B) mounted to a second holding apparatus 152 (see FIGS. 4A, 5B, 8) of the third pivotal linkage assembly 150 (see FIGS. 4A, 5B, 8).

As further shown in FIG. 8, the system 300 comprises one or more measuring devices 302 (see also FIGS. 4B-5C) coupled to the flexible aerodynamic member 12, such as the rotor blade 12a, to measure the one or more axial loads 64a in the flexible aerodynamic member 12, such as the rotor blade 12a, during the testing 63 (see FIG. 8) of the flexible aerodynamic member 12, such as the rotor blade 12a. As shown in FIG. 8, the one or more measuring devices 302 may comprise one or more strain gauges 302a, axial gauges 302b, sensors 302c, or another suitable measuring device.

Preferably, as shown in FIGS. 4B-5C, the one or more measuring devices 302 may be coupled or attached, either wirelessly or with wires, to the top and/or bottom exterior of the flexible aerodynamic member 12, such as the rotor blade 12a, and to each other. The one or more measuring devices 302 may be wired together to form a bridge, which is aligned to measure the axial loads 64a (see FIG. 8), or centrifugal loads; the vertical load 64c (see FIG. 8); the pitch moment 116a (see FIGS. 4A, 8), or rotation or torque; the flap bending moment 116b (see FIGS. 4A, 8), or strain or bending; or another suitable input, force, or moment. Preferably, the one or more measuring devices 302 (see FIG. 8) are in wired or wireless communication with a control and data collection system 304 (see FIGS. 4B-5D).

As further shown in FIG. 8, the system 300 comprises the control and data collection system 304 coupled to the fixture 10. As shown in FIGS. 4B-5D, the control and data collection system 304 may be connected to the fixture 10 and/or the one or more measuring devices 302 via one or more connectors 303, such as in the form of a wire connector, or another suitable connector. The control and data collection system 304 (see FIGS. 4B-5D) may also be wirelessly connected to the fixture 10 (see FIGS. 4B-5D) and/or the one or more measuring devices 302 (see FIGS. 4B-5D).

The control and data collection system 304 (see FIG. 8) comprises one or more controllers 308 (see FIGS. 4B-5D, 8) for controlling one or more inputs 306 (see FIG. 8) to the fixture 10 (see FIG. 8), such as inputs 306 to the actuators and corresponding load cells of the fixture 10 (see FIGS. 4B-5D), for example, the pitch actuators 114 (see FIGS. 4B, 5D) coupled to the pitch actuator load cells 106 (see FIGS. 4B, 5D), the flap actuators 140 (see FIGS. 4B, 5B) coupled to the flap actuator load cells 138 (see FIGS. 4B, 5B), the chord actuators 166 (see FIGS. 4B, 5C) coupled to the chord actuator load cells 164 (see FIGS. 4B, 5C), the flap reaction link load cells 294 (see FIG. 7) coupled to the flap reaction links 288 (see FIG. 7), the axial actuators 184 (see FIG. 5C) coupled to the axial actuator load cells 190 (see FIG. 5C), and the vertical actuators 192 (see FIG. 5A) coupled to the axial actuator load cells 198 (see FIG. 5A), during the testing 63 (see FIG. 8) of the flexible aerodynamic member 12 (see FIG. 8), such as the rotor blade 12a (see FIG. 8). The inputs 306 (see FIG. 8) may include one or more inputs 306 of one or more loads 64 (see FIG. 8), such as an axial load 64a (see FIG. 8), or centrifugal load, a vertical load 64c (see FIG. 8), or another type of load 64. The inputs 306 (see FIG. 8) may further include one or more inputs 306 of one or more moments 116 (see FIG. 8), such as a pitch moment 116a (see FIG. 8) or rotation or torque, a flap bending moment 116b (see FIG. 8) or strain or bending, or another type of moment 116.

As shown in FIG. 8, the control and data collection system 304 preferably further comprises one or more computers 310 (see also FIGS. 4B-5D). Each of the one or more computers 310 comprises one or more processor devices 312, an operating system 314, and a computer memory 316, and each is preferably configured to run and process one or more computer software programs 318.

The one or more computers 310 (see FIGS. 4B-5D, 8) of the control and data collection system 304 (see FIGS. 4B-5D, 8) preferably collect measurement data 68 (see FIG. 8), such as axial load measurement data 68a (see FIG. 8), or other measurement data, generated during the testing 63 (see FIG. 8), such as load testing, of the flexible aerodynamic member 12 (see FIGS. 4B-5D, 8). The fixture 10 (see FIG. 8) minimizes deflections 66 (see FIG. 8) of an outboard end portion 28 (see FIGS. 4B, 5A), or tip, of the flexible aerodynamic member 12 (see FIG. 8) during the testing 63 (see FIG. 8), to provide an improved accuracy 67 (see FIG. 8) of the measurement data 68 (see FIG. 8), such as the axial load measurement data 68a (see FIG. 8). Preferably, the measurement data 68 (see FIG. 8), such as the axial load measurement data 68a (see FIG. 8), obtained from the one or more measuring devices 302 (see FIG. 8) is used to certify or to qualify the flexible aerodynamic member 12 (see FIG. 8), such as the rotor blade 12a (see FIG. 8), for a flight test 320 (see FIG. 8) of an air vehicle 14 (see FIG. 1), such as a rotorcraft 14a (see FIG. 1).

Figure 9:
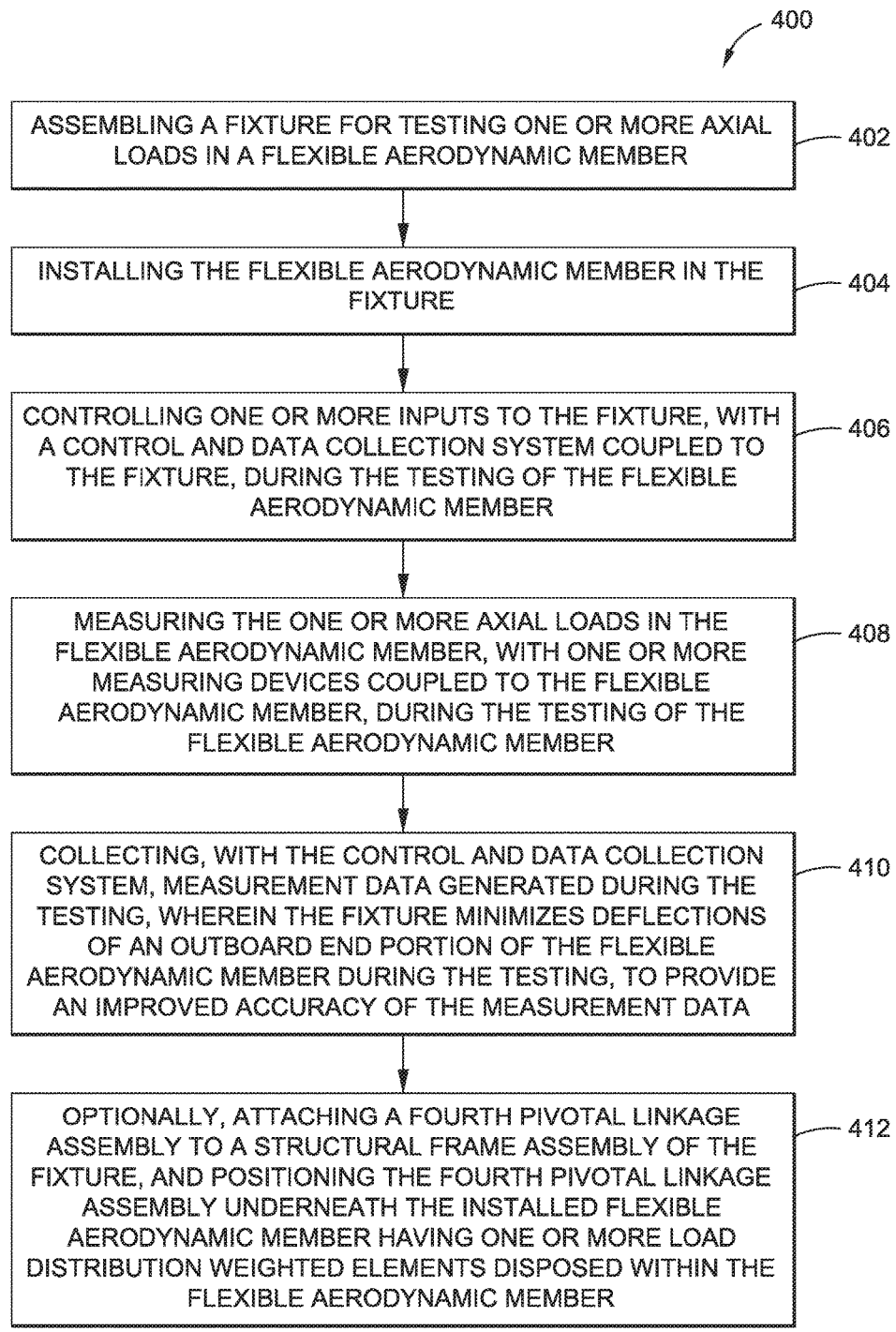
FIG. 9 is an illustration of a flow diagram showing an exemplary embodiment of a method of the disclosure.

Now referring to FIG. 9, FIG. 9 is an illustration of a flow diagram showing an exemplary embodiment of a method 400 of the disclosure for testing 63 (see FIG. 8) one or more axial loads 64a (see FIG. 8) in a flexible aerodynamic member 12 (see FIGS. 4B, 5A, 8).

As shown in FIG. 9, the method 400 comprises steps 402 of assembling a fixture 10, such as in the form of fixture 10a (see FIGS. 4A-4B), or such as in the form of fixture 10b (see FIGS. 5A-5B), for testing 63 (see FIG. 8) one or more axial loads 64a (see FIG. 8) in a flexible aerodynamic member 12 (see FIGS. 4B, 5A, 8), such as a rotor blade 12a (see FIGS. 4B, 5A, 8). The fixture 10 (see FIGS. 4A-5D, 8), such as in the form of fixture 10a (see FIGS. 4A-4B, 8), and such as in the form of fixture 10b (see FIGS. 5A-5B, 8), comprises the structural frame assembly 70 (see FIGS. 4A-5D, 8) having the first end portion 72 (see FIGS. 4A-5D, 8), the second end portion 74 (see FIGS. 4A-5D, 8), and the intermediate portion 76 (see FIGS. 4A-5D, 8) between the first end portion 72 and the second end portion 74.

As discussed in detail above, the fixture 10 (see FIGS. 4A-5D, 8), such as in the form of fixture 10a (see FIGS. 4A-4B, 8), and such as in the form of fixture 10b (see FIGS. 5A-5B, 8), further comprises the first pivotal linkage assembly 90 (see FIGS. 4A-5C, 8) attached to the first end portion 72. The first pivotal linkage assembly 90 is pivotable about the pitch axis 92 (see FIGS. 4A-4B, 5A, 8) and is coupled to the axial reaction member 108 (see FIGS. 4A-5C, 8).

The step 402 (see FIG. 9) of assembling the fixture 10 (see FIGS. 4A-5D, 8), such as in the form of fixture 10a (see FIGS. 4A-4B, 8), and such as in the form of fixture 10b (see FIGS. 5A-5B, 8), further comprises assembling the first pivotal linkage assembly 90 (see FIGS. 4A-5C, 8) comprising the first pivot arm assembly 94 (see FIGS. 4A-5C, 8) pivotally coupled to the first pin joint 96 (see FIGS. 4A-5C, 8). The first pivot arm assembly 94 (see FIGS. 4A-5C, 8) comprises the horizontal arm 98 (see FIGS. 4B, 5A) coupled to the pair of pitch actuator lugs 104 (see FIGS. 4B, 5A) and the pair of pitch actuator load cells 106 (see FIGS. 4A-5B, 8). The first pivot arm assembly 94 (see FIGS. 4B, 5A, 8) further comprises the first pin joint link 100 (see FIGS. 4B, 5A) attached to the horizontal arm 98. The first pivot arm assembly 94 (see FIGS. 4B, 5A, 8) further comprises the pair of side plates 102 (see FIGS. 4B, 5A) attached to the first pin joint link 100 (see FIGS. 4B, 5A). The fixture 10 (see FIGS. 4A-5D, 8), such as in the form of fixture 10a (see FIGS. 4A-4B, 8), and such as in the form of fixture 10b (see FIGS. 5A-5B, 8), further comprises the pair of pitch actuators 114 (see FIGS. 4B, 5A, 8) operably coupled to the first pivotal linkage assembly 90 (see FIGS. 4B, 5A, 8), to apply the pitch moment 116a (see FIG. 8) to the first pivotal linkage assembly 90.

The fixture 10 (see FIGS. 4A-5D, 8), such as in the form of fixture 10a (see FIGS. 4A-4B, 8), and such as in the form of fixture 10b (see FIGS. 5A-5B, 8), further comprises the second pivotal linkage assembly 120 (see FIGS. 4B, 5A, 8) attached to the first pivotal linkage assembly 90 (see FIGS. 4B, 5A, 8). The second pivotal linkage assembly 120 (see FIGS. 4B, 5A, 8) is pivotable about the flap axis 122 (see FIGS. 4B, 5A, 8). The flap axis 122 (see FIGS. 4B, 5A, 8) is perpendicular to the pitch axis 92 (see FIGS. 4A-4B, 5A, 8).

The fixture 10 (see FIGS. 4A-5D, 8), such as in the form of fixture 10a (see FIGS. 4A-4B, 8), and such as in the form of fixture 10b (see FIGS. 5A-5B, 8), further comprises the pair of flap actuators 140 (see FIGS. 4B, 5A, 8) operably coupled to the second pivotal linkage assembly 120 (see FIGS. 4B, 5A, 8), to apply the flap bending moment 116b (see FIG. 8) to the second pivotal linkage assembly 120.

The step 402 (see FIG. 9) of assembling the fixture 10 (see FIGS. 4A-5D, 8), such as in the form of fixture 10a (see FIGS. 4A-4B, 8), and such as in the form of fixture 10b (see FIGS. 5A-5B, 8), further comprises assembling the second pivotal linkage assembly 120 (see FIGS. 4B, 5A, 8) comprising the second pivot arm assembly 130 (see FIGS. 4B, 5A, 8) pivotally coupled to the second pin joint 132 (see FIGS. 4B, 5A, 8). The second pivot arm assembly 130 (see FIGS. 4B, 5A, 8) comprises the pair of vertical arms 134 (see FIGS. 4B, 5A) each attached via the second pin joint 132 (see FIGS. 4B, 5A, 8) to the first pivotal linkage assembly 90 (see FIGS. 4B, 5A, 8). The second pivot arm assembly 130 (see FIGS. 4B, 5A, 8) further comprises the pair of flap link assemblies 136 (see FIGS. 4B, 5A) attached to the pair of vertical arms 134 (see FIGS. 4B, 5A). The second pivot arm assembly 130 (see FIGS. 4B, 5A, 8) further comprises the pair of flap actuator load cells 138 (see FIGS. 4B, 5A, 8) coupled to the pair of flap link assemblies 136 (see FIGS. 4B, 5A).

The fixture 10 (see FIGS. 4A-5D, 8), such as in the form of fixture 10a (see FIGS. 4A-4B, 8), and such as in the form of fixture 10b (see FIGS. 5A-5B, 8), further comprises the third pivotal linkage assembly 150 (see FIGS. 4B, 5A, 8) attached to the second end portion 74 (see FIGS. 4B, 5A, 8). The third pivotal linkage assembly 150 (see FIGS. 4B, 5A, 8) is pivotable about the pitch axis 92 (see FIGS. 4A-4B, 5A, 8). The fixture 10 (see FIGS. 4A-5D, 8), such as in the form of fixture 10a (see FIGS. 4A-4B, 8), and such as in the form of fixture 10b (see FIGS. 5A-5B, 8), further comprises the pair of chord actuators 166 (see FIGS. 4B, 7, 8) operably coupled to the third pivotal linkage assembly 150 (see FIGS. 4B, 5A, 7), to apply an axial load 64a (see FIG. 8) to the flexible aerodynamic member 12 (see FIGS. 4B, 5A, 7) via the third pivotal linkage assembly 150.

The step 402 (see FIG. 9) of assembling the fixture 10 (see FIGS. 4A-5D, 8), such as in the form of fixture 10a (see FIGS. 4A-4B, 8), and such as in the form of fixture 10b (see FIGS. 5A-5B, 8), further comprises assembling the third pivotal linkage assembly 150 (see FIGS. 4B, 5A, 8) comprising the mounting assembly 154 (see FIGS. 4B, 5A, 8), the pair of flap reaction link assemblies 160 (see FIGS. 4B, 5A, 8) attached to the mounting assembly 154, the pair of chord actuator lug assemblies 162 (see FIGS. 4B, 5A, 8) attached to the mounting assembly 154, and the pair of chord actuator load cells 164 (see FIGS. 4B, 5A, 8) coupled to the pair of chord actuator lug assemblies 162, where the pair of chord actuators 166 is operably coupled to the pair of chord actuator load cells 164, respectively.

As further shown in FIG. 9, the method 400 comprises step 404 of installing the flexible aerodynamic member 12 in the fixture 10 (see FIGS. 4A-5D, 8), such as in the form of fixture 10a (see FIGS. 4A-4B, 8), or such as in the form of fixture 10b (see FIGS. 5A-5B, 8). The flexible aerodynamic member 12 (see FIGS. 4B, 5A, 8) has the inboard end portion 24 (see FIGS. 4B, 5A) and the outboard end portion 28 (see FIGS. 4B, 5A). The inboard end portion 24 is mounted to the first holding apparatus 124 (see FIGS. 4B, 5A, 8) of the second pivotal linkage assembly 120 (see FIGS. 4B, 5A, 8). The outboard end portion 28 is mounted to the second holding apparatus 152 (see FIGS. 4B, 5A, 8) of the third pivotal linkage assembly 150 (see FIGS. 4B, 5A, 8). The step 404 (see FIG. 9) of installing further comprises installing the flexible aerodynamic member 12 (see FIGS. 4B, 5A, 8) comprising the rotor blade 12a (see FIGS. 4B, 5A, 8) of an air vehicle 14 (see FIG. 1), such as a rotorcraft 14a (see FIG. 1).

As further shown in FIG. 9, the method 400 comprises step 406 of controlling one or more inputs 306 (see FIG. 8) to the fixture 10 (see FIGS. 4A-5D, 8), such as in the form of fixture 10a (see FIGS. 4A-4B, 8), or such as in the form of fixture 10b (see FIGS. 5A-5B, 8), with the control and data collection system 304 (see FIGS. 4B-5D, 8) coupled to the fixture 10 (see FIGS. 4A-5D, 8), such as in the form of fixture 10a (see FIGS. 4A-4B, 8), or such as in the form of fixture 10b (see FIGS. 5A-5B, 8), during the testing 63 (see FIG. 8) of the flexible aerodynamic member 12, such as the rotor blade 12a. The control and data collection system 304 (see FIGS. 4B-5D, 8) preferably comprises one or more controllers 308 (see FIGS. 4B-5D, 8) for controlling one or more inputs 306 (see FIG. 8) to the fixture 10 (see FIGS. 4A-5D, 8), such as in the form of fixture 10a (see FIGS. 4A-4B, 8), or such as in the form of fixture 10b (see FIGS. 5A-5B, 8), during the testing 63 (see FIG. 8) of the flexible aerodynamic member 12 (see FIG. 8), such as the rotor blade 12a (see FIG. 8). The inputs 306 (see FIG. 8) may include one or more inputs 306 (see FIG. 8) of one or more loads 64 (see FIG. 8), such as an axial load 64a (see FIG. 8), a vertical load 64c (see FIG. 8), or another type of load 64. The inputs 306 (see FIG. 8) may further include one or more inputs 306 (see FIG. 8) of one or more moments 116 (see FIG. 8), such as a pitch moment 116a (see FIG. 8), a flap bending moment 116b (see FIG. 8), or another type of moment 116.

As used herein, "moment" means a moment of a force that causes an object to rotate about a fixed reference point or axis, and is the product of the force and the distance from the fixed reference point or axis. For example, moment equals force times distance (M=(F)(d)), where the force is typically measured in newtons (N) and the distance is typically measured as the perpendicular distance in meters (m). A moment arm is the perpendicular distance between the axis of rotation of the force and the center of the moments.

As further shown in FIG. 9, the method 400 comprises step 408 of measuring the one or more axial loads 64a (see FIG. 8) in the flexible aerodynamic member 12 (see FIGS. 4B-5C, 8), such as the rotor blade 12a (see FIGS. 4B-5C, 8), with one or more measuring devices 302 (see FIGS. 4B-5C, 8) coupled to the flexible aerodynamic member 12, such as the rotor blade 12a, during the testing 63 (see FIG. 8) of the flexible aerodynamic member 12, such as the rotor blade 12a. The step 408 of measuring further comprises measuring with one or more measuring devices 302 (see FIGS. 4B-5C, 8) comprising one or more strain gauges 302a (see FIG. 8), one or more axial gauges 302b (see FIG. 8), one or more sensors 302c (see FIG. 8), or other suitable measuring devices. Preferably, as shown in FIGS. 4B-5C, the one or more measuring devices 302 may be coupled or attached, either wirelessly or with wires, to the exterior of the flexible aerodynamic member 12, such as the rotor blade 12a. Preferably, the one or more measuring devices 302 (see FIGS. 4B-5D, 8) are in wired or wireless communication with the control and data collection system 304 (see FIGS. 4B-5D, 8).

As further shown in FIG. 9, the method 400 comprises step 410 of collecting, with the control and data collection system 304 (see FIGS. 4B-5C, 8), measurement data 68 (see FIG. 8) generated during the testing 63 (see FIG. 8). As shown in FIGS. 4B-5D, 8, the control and data collection system 304 comprises one or more computers 310 that may be used to collect the measurement data 68 (see FIG. 8), generated during the testing 63 (see FIG. 8), such as load testing, of the flexible aerodynamic member 12 (see FIGS. 4B-5D, 8), such as the rotor blade 12a. The fixture 10 (see FIGS. 4A-5D, 8), such as in the form of fixture 10a (see FIGS. 4A-4B, 8), and such as in the form of fixture 10b (see FIGS. 5A-5B, 8), preferably minimizes deflections 66 (see FIG. 8) of the outboard end portion 28 (see FIGS. 4B, 5A), or tip, of the flexible aerodynamic member 12, such as the rotor blade 12a, during the testing 63 (see FIG. 8), to provide an improved accuracy 67 (see FIG. 8) of the measurement data 68 (see FIG. 8). The step 410 of collecting further comprises collecting measurement data 68 (see FIG. 8) comprising axial load measurement data 68a (see FIG. 8), or other suitable measurement data, from the one or more measuring devices 302 (see FIGS. 4B-5C, 8), to certify or to qualify the flexible aerodynamic member 12, such as the rotor blade 12a, for a flight test 320 (see FIG. 8) of an air vehicle 14 (see FIG. 1), such as a rotorcraft 14a (see FIG. 1).

As further shown in FIG. 9, the method 400 may further comprise the optional step 412 of attaching the fourth pivotal linkage assembly 180 (see FIGS. 5A-5D, 8) to the intermediate portion 76 (see FIGS. 5A-5D, 8) of the structural frame assembly 70 (see FIGS. 5A-5D, 8), in connection with the step 402 (see FIG. 9) of assembling the fixture 10 (see FIGS. 5A-5D, 8), such as assembling the fixture 10b (see FIGS. 5A-5D, 8). The optional step 412 (see FIG. 9) comprises positioning the fourth pivotal linkage assembly 180 (see FIGS. 5A-5B, 8) underneath the installed flexible aerodynamic member 12 (see FIGS. 5A-5D, 8), such as the rotor blade 12a (see FIGS. 5A-5D, 8), where the flexible aerodynamic member 12, such as the rotor blade 12a, has one or more load distribution weighted elements 182 (see FIGS. 5A-5D, 8) disposed within the flexible aerodynamic member 12, such as the rotor blade 12a.

As discussed in detail above, the fourth pivotal linkage assembly 180 (see FIGS. 5A-5D, 8) comprises the pair of vertical actuators 192 (see FIGS. 5A-5B, 8) operably coupled via the pair of vertical actuator load cells 198 (see FIGS. 5A-5B, 8), and via the pair of vertical actuator link assemblies 220 (see FIGS. 5A-5B, 8), to apply vertical load 64c (see FIG. 8) to the one or more load distribution weighted elements 182 (see FIGS. 5A-5B, 8) of the flexible aerodynamic member 12 (see FIGS. 5A-5B, 8), such as the rotor blade 12a (see FIGS. 5A-5B, 8). The fourth pivotal linkage assembly 180 (see FIGS. 5A-5B, 8) further comprises the pair of axial actuators 184 (see FIGS. 5A-5B, 8) operably coupled via the pair of axial actuator load cells 190 (see FIGS. 5A-5B, 8), via the pair of axial actuator link assemblies 200 (see FIGS. 5A-5B, 8), and via the pair of vertical actuator link assemblies 220 (see FIGS. 5A-5B, 8), to apply axial load 64a (see FIG. 8) to the one or more load distribution weighted elements 182 (see FIGS. 5A-5B, 8) of the flexible aerodynamic member 12 (see FIGS. 5A-5B, 8), such as the rotor blade 12a (see FIGS. 5A-5B, 8).

Disclosed embodiments of the fixture 10 (see FIGS. 4A-5D), the system 300 (see FIGS. 4B-5D, 8), and the method 400 (see FIG. 9) allow for a more controlled testing 63 (see FIG. 8) of loads 64 (see FIG. 8), such as axial loads 64a (see FIG. 8), also referred to as centrifugal loads, in a flexible aerodynamic member 12 (see FIGS. 1, 4B-5C, 8), such as a rotor blade 12a (see FIGS. 1, 4B-5C, 8), or other suitable blade or aerodynamic member, used in an air vehicle 14 (see FIG. 1), such as a rotorcraft 14a (see FIG. 1). In addition, disclosed embodiments of the fixture 10 (see FIGS. 4A-5D), the system 300 (see FIGS. 4B-5D, 8), and the method 400 (see FIG. 9) control displacements and minimize deflections 66 (see FIG. 8) of the outboard end portion 28 (see FIGS. 4B, 5A), or tip, of the flexible aerodynamic member 12 (see FIGS. 4B-5C, 8), such as the rotor blade 12a (see FIGS. 4B-5C, 8), that may be cambered and twisted, during testing 63 (see FIG. 8), and where axial loads 64a (see FIG. 8) are introduced. By controlling displacements and minimizing deflections 66 (see FIG. 8), a user 62 (see FIGS. 4B-5D), the user 62 (see FIGS. 4B-5D) avoids having to control a deflected structure, which may be difficult. Moreover, controlled displacements and minimized deflections 66 may provide an improved accuracy 67 (see FIG. 8) and precision of measurement data 68 (see FIG. 8), such as axial load measurement data 68a (see FIG. 8), obtained by one or more measuring devices 302 (see FIG. 8) coupled to the flexible aerodynamic member 12 during testing 63 (see FIG. 8).

Further, disclosed embodiments of the fixture 10 (see FIGS. 4A-5D), the system 300 (see FIGS. 4B-5D, 8), and the method 400 (see FIG. 9) allow for testing of longer rotor blades, as compared to known testing fixtures, systems, and methods, since deflections 66 of the outboard end portion 28 (see FIGS. 4B, 5A), or tip, of the rotor blade 12a are minimized, and also allow for the accommodation of greater than twelve (12) inches of deflection 66 (see FIG. 8) without introducing unwanted loads or moments or other undesirable effects. Disclosed embodiments of the fixture 10 (see FIGS. 4A-5D), the system 300 (see FIGS. 4B-5D, 8), and the method 400 (see FIG. 9) maintain the application or input of loads 64 (see FIG. 8) without introducing unwanted loads or moments and undesirable displacements or offset effects into the outboard end portion 28 (see FIGS. 4B, 5A), or tip, of the rotor blade that may not be representative of the actual loads to which the rotor blade 12a may be subjected when in service. In addition, disclosed embodiments of the fixture 10 (see FIGS. 4A-5D), the system 300 (see FIGS. 4B-5D, 8), and the method 400 (see FIG. 9) provide the ability to isolate the loading, such as the axial loading, during testing 63 (see FIG. 8), which, in turn, may enable design and manufacture of a lighter and more robust rotary blade structure.

The measurement data 68 (see FIG. 8), such as axial load measurement data 68a (see FIG. 8), obtained by the one or more measuring devices 302 (see FIG. 8) during testing 63 (see FIG. 8), may preferably be used to certify or qualify the flexible aerodynamic member 12 (see FIGS. 1, 4B-5C, 8), such as the rotor blade 12a (see FIGS. 1, 4B-5C, 8) for flight tests 320 (see FIG. 8), and/or to confirm the flexible aerodynamic member 12 (see FIGS. 1, 4B-5C, 8), such as the rotor blade 12a (see FIGS. 1, 4B-5C, 8), performs as required. Thus, the disclosed embodiments of the fixture 10 (see FIGS. 4A-5D), the system 300 (see FIGS. 4B-5D, 8), and the method 400 (see FIG. 9) enable the certification of new rotor blade structures. Moreover, the improved accuracy 67 (see FIG. 8) and precision of the measurement data 68 (see FIG. 8), such as the axial load measurement data 68a (see FIG. 8), obtained by the one or more measuring devices 302 (see FIG. 8) during testing 63 (see FIG. 8), may be used to make the structure of the flexible aerodynamic member 12 (see FIGS. 1, 4B-5C, 8), such as the rotor blade 12a (see FIGS. 1, 4B-5C, 8), more efficient. The fixture 10 (see FIGS. 4A-5D), the system 300 (see FIGS. 4B-5D, 8), and the method 400 (see FIG. 9) allow for the measurement of axial load measurement data 68a (see FIG. 8) whish is useful in establishing flight operational limits for a rotor blade 12a.

Moreover, in one embodiment of the fixture 10b (see FIGS. 5A-5D), the system 300 (see FIGS. 5A-5D), and the method 400 (see FIG. 9), a fourth pivotal linkage assembly 180 (see FIGS. 5A-5D) is used for testing of flexible aerodynamic members 12 (see FIGS. 5A-5C, 8), such as rotor blades 12a (see FIGS. 5A-5C, 8), having one or more load distribution weighted elements 182 (see FIGS. 5A-5C, 8), or weight pockets, disposed within the flexible aerodynamic members 12 (see FIGS. 5A-5C, 8), such as rotor blades 12a (see FIGS. 5A-5C, 8). This embodiment allows for testing of rotor blades 12a having one or more load distribution weighted elements 182 (see FIGS. 5A-5C, 8), or weight pockets, by virtue of the fourth pivotal linkage assembly 180 (see FIGS. 5A-5D) added to the structural frame assembly 70 (see FIGS. 5A-5D). Such load distribution weighted elements 182 (see FIGS. 5A-5C, 8), or weight pockets, may be required in certain rotor blades, depending on the shape of the blade, to balance the rotor blade during flight, and the fixture 10b (see FIGS. 5A-5D), the system 300 (see FIGS. 5A-5D), and the method 400 (see FIG. 9), are able to drive a vertical load 64c (see FIG. 8) into the load distribution weighted elements 182 (see FIGS. 5A-5C, 8), while the rotor blade 12a is being tested for one or more axial loads 64a (see FIG. 8), with minimal deflections 66 (see FIG. 8) of the outboard end portion 28 (see FIG. 5A), or tip, of the rotor blade 12a.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation. Any claimed embodiment of the disclosure does not necessarily include all of the embodiments of the disclosure.

What is claimed is:

1. A fixture for testing one or more axial loads in a flexible aerodynamic member, the fixture comprising:
    a structural frame assembly having a first end portion, a second end portion, and an intermediate portion between the first end portion and the second end portion;
    a first pivotal linkage assembly attached to the first end portion, the first pivotable linkage assembly pivotable about a pitch axis and coupled to an axial reaction member;
    a pair of pitch actuators operably coupled to the first pivotal linkage assembly, to apply a pitch moment to the first pivotal linkage assembly;
    a second pivotal linkage assembly attached to the first pivotal linkage assembly, the second pivotal linkage assembly pivotable about a flap axis, the flap axis being perpendicular to the pitch axis, and the second pivotal linkage assembly having a first holding apparatus that holds an inboard end portion of the flexible aerodynamic member;
    a pair of flap actuators operably coupled to the second pivotal linkage assembly, to apply a flap bending moment to the second pivotal linkage assembly;
    a third pivotal linkage assembly attached to the second end portion of the structural frame assembly, the third pivotal linkage assembly pivotable about the pitch axis, and having a second holding apparatus that holds an outboard end portion of the flexible aerodynamic member; and
    a pair of chord actuators operably coupled to the third pivotal linkage assembly to apply axial load to the flexible aerodynamic member, via the third pivotal linkage assembly,
    wherein the fixture minimizes deflections of the outboard end portion of the flexible aerodynamic member during testing of the one or more axial loads in the flexible aerodynamic member, to provide an improved accuracy of axial load measurement data.

2. The fixture of claim 1 further comprising:
    a fourth pivotal linkage assembly attached to the intermediate portion of the structural frame assembly, the fourth pivotal linkage assembly being positioned underneath the flexible aerodynamic member, when the flexible aerodynamic member is mounted to, and positioned between, the first holding apparatus and the second holding apparatus, and wherein the flexible aerodynamic member has one or more load distribution weighted elements disposed within the flexible aerodynamic member, the fourth pivotal linkage assembly comprising:
        a pair of vertical actuators operably coupled via a pair of vertical actuator load cells and via a pair of vertical actuator link assemblies, to apply vertical load to the one or more load distribution weighted elements of the flexible aerodynamic member; and a pair of axial actuators operably coupled via a pair of axial actuator load cells, via a pair of axial actuator link assemblies, and via the pair of vertical actuator link assemblies, to apply axial load to the one or more load distribution weighted elements of the flexible aerodynamic member.

3. The fixture of claim 1 wherein the first pivotal linkage assembly comprises a first pivot arm assembly pivotally coupled to a first pin joint, the first pivot arm assembly comprising:
a horizontal arm coupled to a pair of pitch actuator lugs and a pair of pitch actuator load cells;
a first pin joint link attached to the horizontal arm; and
a pair of side plates attached to the first pin joint link.

4. The fixture of claim 3 wherein the first pin joint comprises a pitch shaft having a first guide end portion and a second reaction end portion, the first guide end portion coupled to a retaining apparatus, and the second reaction end portion coupled to the axial reaction member.

5. The fixture of claim 1 wherein the second pivotal linkage assembly comprises a second pivot arm assembly pivotally coupled to a second pin joint, the second pivot arm assembly comprising:
a pair of vertical arms, each attached via the second pin joint to the first pivotal linkage assembly;
a pair of flap link assemblies attached to the pair of vertical arms; and
a pair of flap actuator load cells coupled to the pair of flap link assemblies.

6. The fixture of claim 1 wherein the third pivotal linkage assembly comprises:
a mounting assembly;
a pair of flap reaction link assemblies attached to the mounting assembly;
a pair of chord actuator lug assemblies attached to the mounting assembly; and
a pair of chord actuator load cells coupled to the pair of chord actuator lug assemblies, wherein the pair of chord actuators is operably coupled to the pair of chord actuator load cells, respectively.

7. The fixture of claim 1 wherein the structural frame assembly further comprises:
a plurality of vertical frame beams;
a plurality of horizontal frame beams perpendicular to the plurality of vertical frame beams;
a plurality of cross support structures attached to one or more of the plurality of vertical frame beams and to one or more of the plurality of horizontal frame beams;
a plurality of platform assemblies attached to one or more of the plurality of vertical frame beams and to one or more of the plurality of horizontal frame beams; and
a diagonal brace attached at the second end portion.

8. The fixture of claim 1 wherein the flexible aerodynamic member comprises a rotor blade of a rotorcraft.

9. The fixture of claim 8 wherein the rotor blade is cambered and twisted during testing of the one or more axial loads.

10. A system for testing one or more axial loads in a flexible aerodynamic member, the system comprising:
a fixture comprising:
a structural frame assembly having a first end portion, a second end portion, and an intermediate portion between the first end portion and the second end portion;
a first pivotal linkage assembly attached to the first end portion, the first pivotal linkage assembly pivotable about a pitch axis and coupled to an axial reaction member;
a pair of pitch actuators operably coupled to the first pivotal linkage assembly, to apply a pitch moment to the first pivotal linkage assembly;
a second pivotal linkage assembly attached to the first pivotal linkage assembly, the second pivotal linkage assembly pivotable about a flap axis, the flap axis being perpendicular to the pitch axis;
a pair of flap actuators operably coupled to the second pivotal linkage assembly, to apply a flap bending moment to the second pivotal linkage assembly;
a third pivotal linkage assembly attached to the second end portion, the third pivotal linkage assembly pivotable about the pitch axis; and
a pair of chord actuators operably coupled to the third pivotal linkage assembly, to apply axial load to the flexible aerodynamic member, via the third pivotal linkage assembly;
the flexible aerodynamic member having an inboard end portion and an outboard end portion, the flexible aerodynamic member installed in the fixture with the inboard end portion mounted to a first holding apparatus of the second pivotal linkage assembly, and with the outboard end portion mounted to a second holding apparatus of the third pivotal linkage assembly;
one or more measuring devices coupled to the flexible aerodynamic member, to measure the one or more axial loads during the testing of the flexible aerodynamic member; and
a control and data collection system coupled to the fixture to control one or more inputs to the fixture during the testing of the flexible aerodynamic member, and to collect measurement data generated during the testing, including axial load measurement data, wherein the fixture minimizes deflections of the outboard end portion of the flexible aerodynamic member during the testing, to provide an improved accuracy of the axial load measurement data.

11. The system of claim 10 wherein the fixture further comprises:
a fourth pivotal linkage assembly attached to the intermediate portion of the structural frame assembly, the fourth pivotal linkage assembly being positioned underneath the flexible aerodynamic member, when the flexible aerodynamic member is mounted to, and positioned between, the first holding apparatus and the second holding apparatus, and wherein the flexible aerodynamic member has one or more load distribution weighted elements disposed within the flexible aerodynamic member, the fourth pivotal linkage assembly comprising:
a pair of vertical actuators operably coupled via a pair of vertical actuator load cells and via a pair of vertical actuator link assemblies, to apply vertical load to the one or more load distribution weighted elements of the flexible aerodynamic member; and
a pair of axial actuators operably coupled via a pair of axial actuator load cells, via a pair of axial actuator link assemblies, and via the pair of vertical actuator link assemblies, to apply axial load to the one or more load distribution weighted elements of the flexible aerodynamic member.

12. The system of claim 10 wherein the first pivotal linkage assembly comprises a first pivot arm assembly pivotally coupled to a first pin joint, the first pivot arm assembly comprising:
  a horizontal arm coupled to a pair of pitch actuator lugs and a pair of pitch actuator load cells;
  a first pin joint link attached to the horizontal arm; and
  a pair of side plates attached to the first pin joint link.

13. The system of claim 10 wherein the second pivotal linkage assembly comprises a second pivot arm assembly pivotally coupled to a second pin joint, the second pivot arm assembly comprising:
  a pair of vertical arms, each attached via the second pin joint to the first pivotal linkage assembly;
  a pair of flap link assemblies attached to the pair of vertical arms; and
  a pair of flap actuator load cells coupled to the pair of flap link assemblies.

14. The system of claim 10 wherein the third pivotal linkage assembly comprises:
  a mounting assembly;
  a pair of flap reaction link assemblies attached to the mounting assembly;
  a pair of chord actuator lug assemblies attached to the mounting assembly; and
  a pair of chord actuator load cells coupled to the pair of chord actuator lug assemblies, wherein the pair of chord actuators is operably coupled to the pair of chord actuator load cells, respectively.

15. The system of claim 10 wherein the flexible aerodynamic member comprises a rotor blade of a rotorcraft, and the one or more measuring devices comprise one of, strain gauges, axial gauges, and sensors, and further wherein the axial load measurement data obtained from the one or more measuring devices is used to certify or to qualify the rotor blade for a flight test of the rotorcraft.

16. A method for testing one or more axial loads in a flexible aerodynamic member, the method comprising the steps of:
  assembling a fixture for testing one or more axial loads in the flexible aerodynamic member, the fixture comprising:
    a structural frame assembly having a first end portion, a second end portion, and an intermediate portion between the first end portion and the second end portion;
    a first pivotal linkage assembly attached to the first end portion, the first pivotal linkage assembly pivotable about a pitch axis and coupled to an axial reaction member;
    a pair of pitch actuators operably coupled to the first pivotal linkage assembly, to apply a pitch moment to the first pivotal linkage assembly;
    a second pivotal linkage assembly attached to the first pivotal linkage assembly, the second pivotal linkage assembly pivotable about a flap axis, the flap axis being perpendicular to the pitch axis;
    a pair of flap actuators operably coupled to the second pivotal linkage assembly, to apply a flap bending moment to the second pivotal linkage assembly;
    a third pivotal linkage assembly attached to the second end portion, the third pivotal linkage assembly pivotable about the pitch axis; and
    a pair of chord actuators operably coupled to the third pivotal linkage assembly, to apply axial load to the flexible aerodynamic member, via the third pivotal linkage assembly;
  installing the flexible aerodynamic member in the fixture, the flexible aerodynamic member having an inboard end portion and an outboard end portion, the inboard end portion mounted to a first holding apparatus of the second pivotal linkage assembly, and the outboard end portion mounted to a second holding apparatus of the third pivotal linkage assembly;
  controlling one or more inputs to the fixture, with a control and data collection system coupled to the fixture, during the testing of the flexible aerodynamic member;
  measuring the one or more axial loads in the flexible aerodynamic member, with one or more measuring devices coupled to the flexible aerodynamic member, during the testing of the flexible aerodynamic member; and
  collecting, with the control and data collection system, measurement data generated during the testing, wherein the fixture minimizes deflections of the outboard end portion of the flexible aerodynamic member during the testing to provide an improved accuracy of the measurement data.

17. The method of claim 16 wherein assembling the fixture further comprises step of attaching a fourth pivotal linkage assembly to the intermediate portion of the structural frame assembly, and positioning the fourth pivotal linkage assembly underneath the installed flexible aerodynamic member having one or more load distribution weighted elements disposed within the flexible aerodynamic member, the fourth pivotal linkage assembly comprising:
  a pair of vertical actuators operably coupled via a pair of vertical actuator load cells and via a pair of vertical actuator link assemblies, to apply vertical load to the one or more load distribution weighted elements of the flexible aerodynamic member; and
  a pair of axial actuators operably coupled via a pair of axial actuator load cells, via a pair of axial actuator link assemblies, and via the pair of vertical actuator link assemblies, to apply axial load to the one or more load distribution weighted elements of the flexible aerodynamic member.

18. The method of claim 16 wherein assembling the fixture further comprises assembling the first pivotal linkage assembly comprising a first pivot arm assembly pivotally coupled to a first pin joint, the first pivot arm assembly comprising:
  a horizontal arm coupled to a pair of pitch actuator lugs and a pair of pitch actuator load cells;
  a first pin joint link attached to the horizontal arm; and
  a pair of side plates attached to the first pin joint link.

19. The method of claim 16 wherein assembling the fixture further comprises assembling the second pivotal linkage assembly comprising a second pivot arm assembly pivotally coupled to a second pin joint, the second pivot arm assembly comprising:
  a pair of vertical arms, each attached via the second pin joint to the first pivotal linkage assembly;
  a pair of flap link assemblies attached to the pair of vertical arms; and
  a pair of flap actuator load cells coupled to the pair of flap link assemblies.

20. The method of claim 16 wherein assembling the fixture further comprises assembling the third pivotal linkage assembly comprising:
  a mounting assembly;
  a pair of flap reaction link assemblies attached to the mounting assembly;

a pair of chord actuator lug assemblies attached to the mounting assembly; and a pair of chord actuator load cells coupled to the pair of chord actuator lug assemblies, wherein the pair of chord actuators is operably coupled to the pair of chord actuator load cells, respectively.

21. The method of claim 16 wherein installing further comprises installing the flexible aerodynamic member comprising a rotor blade of a rotorcraft, and wherein measuring further comprises measuring with one or more measuring devices comprising one of, strain gauges, axial gauges, and sensors, and wherein collecting further comprises collecting measurement data comprising axial load measurement data, from the one or more measuring devices to certify or to qualify the rotor blade for a flight test of the rotorcraft.

* * * * *